US008137977B2

(12) United States Patent
Kaddurah-Daouk et al.

(10) Patent No.: US 8,137,977 B2
(45) Date of Patent: Mar. 20, 2012

(54) LIPIDOMIC APPROACHES TO DETERMINING DRUG RESPONSE PHENOTYPES IN CARDIOVASCULAR DISEASE

(75) Inventors: Rima F. Kaddurah-Daouk, Belmont, MA (US); Michelle M. Wiest, Knights Landing, CA (US); Steven M. Watkins, Sacramento, CA (US); Rebecca Ann Baillie, Woodland, CA (US); Madhumita Patnaik, Agoura Hills, CA (US); K. Ranga Rama Krishnan, Chapel Hill, NC (US); Richard M. Weinshilboum, Rochester, MN (US); Ronald M. Krauss, Berkeley, CA (US)

(73) Assignees: Children's Hospital & Research Center at Oakland, Oakland, CA (US); Duke University, Durham, NC (US); Lipomics Technologies, Inc., West Sacramento, CA (US); Mayo Foundation for Medical Education and Research, Rochester, MN (US)

( * ) Notice: Subject to any disclaimer, the term of this patent is extended or adjusted under 35 U.S.C. 154(b) by 230 days.

(21) Appl. No.: 12/257,957

(22) Filed: Oct. 24, 2008

(65) Prior Publication Data
US 2009/0197242 A1 Aug. 6, 2009

Related U.S. Application Data

(60) Provisional application No. 60/985,805, filed on Nov. 6, 2007.

(51) Int. Cl.
*G01N 33/92* (2006.01)
*C12Q 1/60* (2006.01)
(52) U.S. Cl. ............... 436/71; 436/63; 435/11
(58) Field of Classification Search .......... 436/63, 436/71; 435/4, 11; 424/283.1
See application file for complete search history.

(56) References Cited

U.S. PATENT DOCUMENTS

| 5,006,462 A | 4/1991 | Gattaz |
| 5,198,468 A | 3/1993 | Horrobin |
| 5,516,800 A | 5/1996 | Horrobin |
| 6,596,701 B1 | 7/2003 | Schwartz et al. |
| 7,005,255 B2 * | 2/2006 | Kaddurah-Daouk et al. .... 435/4 |
| 7,015,006 B1 | 3/2006 | Glen et al. |
| 7,329,489 B2 | 2/2008 | Kaddurah-Daouk et al. |
| 7,550,258 B2 | 6/2009 | Kaddurah-Daouk et al. |
| 7,550,260 B2 | 6/2009 | Kaddurah-Daouk et al. |
| 7,553,616 B2 | 6/2009 | Kaddurah-Daouk et al. |
| 7,611,902 B2 * | 11/2009 | Laaksonen et al. ............. 436/63 |
| 7,635,556 B2 | 12/2009 | Kaddurah-Daouk et al. |
| 7,682,783 B2 | 3/2010 | Kaddurah-Daouk et al. |
| 7,682,784 B2 | 3/2010 | Kaddurah-Daouk et al. |
| 2002/0009740 A1 | 1/2002 | Kaddurah-Daouk et al. |
| 2004/0024065 A1 | 2/2004 | Watkins et al. |
| 2004/0126366 A1 | 7/2004 | Kaddurah-Daouk et al. |
| 2004/0143461 A1 | 7/2004 | Watkins |
| 2004/0146853 A1 | 7/2004 | Kaddurah-Daouk et al. |
| 2005/0009005 A1 | 1/2005 | Watkins |
| 2005/0014132 A1 | 1/2005 | Kaddurah-Daouk et al. |
| 2006/0084129 A1 | 4/2006 | Watkins |
| 2006/0088860 A1 | 4/2006 | Watkins et al. |
| 2006/0134676 A1 | 6/2006 | Kaddurah-Daouk et al. |
| 2006/0134677 A1 | 6/2006 | Kaddurah-Daouk et al. |
| 2006/0134678 A1 | 6/2006 | Kaddurah-Daouk et al. |
| 2006/0141550 A1 | 6/2006 | Watkins et al. |
| 2006/0241021 A1 | 10/2006 | Kaddurah-Daouk et al. |
| 2007/0026389 A1 | 2/2007 | Kaddurah-Daouk et al. |
| 2007/0027090 A1 | 2/2007 | Kaddurah-Daouk et al. |
| 2007/0032969 A1 | 2/2007 | Barrett, Jr. et al. |
| 2007/0072203 A1 | 3/2007 | Kaddurah-Daouk et al. |
| 2007/0172820 A1 | 7/2007 | Kaddurah-Daouk et al. |
| 2007/0172885 A1 | 7/2007 | Kaddurah-Daouk et al. |
| 2007/0178599 A1 | 8/2007 | Kaddurah-Daouk et al. |
| 2008/0269188 A1 * | 10/2008 | Chapman et al. ........ 514/210.02 |
| 2009/0017464 A1 | 1/2009 | Kaddurah-Daouk et al. |
| 2009/0221706 A1 | 9/2009 | Kaddurah-Daouk et al. |
| 2009/0280521 A1 | 11/2009 | Kaddurah-Daouk et al. |
| 2009/0305323 A1 * | 12/2009 | Kaddurah-Daouk et al. .. 435/29 |

FOREIGN PATENT DOCUMENTS

| WO | WO 01/78652 A2 | 10/2001 |
| WO | WO 2004/038381 A2 | 5/2004 |
| WO | WO 2006/008656 A2 | 1/2006 |

OTHER PUBLICATIONS

Simon et al. The American Journal of Cardiology Online, Mar. 15, 2006, pp. 843-850.*
Laaksonen et al. PLoS One, issue 1, e97, Dec. 2006, pp. 1-9.*
Atmaca M., "Serum Leptin and Triglyceride Levels in Patients on Treatment With Atypical Antipsychotics", *J Clin Psychiatry* 64:5, May 2003, pp. 598-604.
Atmaca M., et al. "Serum leptin and cholesterol levels in schizophrenic patients with and without suicide attempts", Acta Psychiar Scand 2003: 108 208-214, ISSN 0001-690X, pp. 208-214, Blackwell Munksgaard 2003.
Atmaca, M. Letter to the Editors—Weight gain, serum leptin and triglyceride levels in patients with schizophrenia on antipsychotic treatment with quetiapine, olanzapine and haloperidol, *Schizophrenia Research* 60 (2003) 99-100, Elsevier Science B.V.

(Continued)

Primary Examiner — Maureen Wallenhorst
(74) Attorney, Agent, or Firm — Myers Bigel Sibley & Sajovec, PA

(57) ABSTRACT

The present invention concerns the application of lipidomics to statin treatment for disorders such as cardiovascular disorders. Hence, the invention provides, among other things, a method of correlating a lipid profile with a positive or negative response to a statin treatment regimen by obtaining a lipid profile of a sample from a mammalian subject following commencement of the treatment regimen; and correlating the lipid profile in the sample with a positive or negative response to the treatment regimen. The invention further provides a method of correlating a lipid profile with a positive or negative response to a statin treatment regimen by obtaining a lipid profile of a sample from a mammalian subject before commencement of the treatment regimen; and correlating the lipid profile in the sample with a positive or negative response to the treatment regimen.

59 Claims, 3 Drawing Sheets

OTHER PUBLICATIONS

Barak et al., "Effects of Olanzapine on Lipid Abnormalities in Elderly Psychotic Patients", *Drugs Aging* 2003: 20 (12) Adis Data Information BV 2003, pp. 893-896.

Baymiller et al., "Serum glucose and lipid changes during the course of clozapine treatment: the effect of concurrent β-adrenergic antagonist treatment", *Schizophrenia Research* 59 (2002) 49-57, Elsevier Science B.V.

Beasley et al., "Reductions in cholesterol and synaptic markers in association cortex in mood disorders", *Bipolar Disorders* 2005: 7: 449-455, Blackwell Munksgaard, 2005.

Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study", *Clinical Therapeutics*, vol. 30, No. 12, 2008, pp. 2298-2313.

Brindle et al., "Application of chemometrics to H NMR spectroscopic data to investigate a relationship between human serum metabolic profiles and hypertension", *Analyst*, 2003, 128, 32-36.

Brindle et al., "Rapid and noninvasive diagnosis of the presence and severity of coronary heart disease using H-NMR-based metabonomics", *Nature Medicine*, vol. 8, No. 12, Dec. 2002, pp. 1439-1444.

Caniato et al., "Effect of omega-3 fatty acids on the lipid profile of patients taking clozapine" *Australian and New Zealand Journal of Psychiatry* 2006; 40:691-697.

Casey, "Dyslipidemia and Atypical Antipsychotic Drugs", *J Clin Psychiatry* 2004; 65 (suppl 18) pp. 27-35.

Cholesterol Treatment Trialists' (CTT) Collaborators, "Efficacy and safety of cholesterol-lowering treatment: prospective meta-analysis of data from 90 056 participants in 14 randomised trials of statins", *The Lancet*, vol. 366, Issue 9493, pp. 1267-1278, Oct. 8, 2005.

De Hert et al., "A Case Series: Evaluation of the Metabolic Safety of Aripiprazole" *Schizophrenia Bulletin* doi:10.1093/schbul/sb1037, Published by Oxford University Press on behalf of the Maryland Psychiatric Research Center, pp. 1-8, date unknown.

Dunne, "Metabolites from cerebrospinal fluid in aneurismal subarachnoid haemorrage correlate with vasospasm and clinical outcome: a pattern-recognition $^1$H NMR study", *NMR in Biomedicine*, *NMR Biomed. 2005*; 18:24-33, Published online Sep. 29, 2004 in Wiley InterScience (www.interscience.wiley.com) DOI:10.1002/nbm.918.

Dursun, "The effects of clozapine on levels of total cholesterol and related lipids in serum of patients with schizophrenia: a prospective study", *Journal of Psychiatry & Neuroscience*; Nov. 1999, vol. 24, Issue 5, p. 453, 3p, 1 graph; CMA Media Inc.

Fan, "Higher fasting serum insulin levels are associated with a better psychopathology profile in acutely ill non-diabetic inpatients with schizophrenia", *Schizophrenia Research* 86 (2006) 30-35; doi: 10.1016/j.schres.2006.04.010.

Farooqui et al., "Inhibitors of Brain Phospholipase $A_2$ Activity: Their Neuropharmacological Effects and Therapeutic Importance for the Treatment of Neurologic Disorders", *Pharmacol Review*, 58:591-620, 2006.

Ferno et al., "Antipsychotic drugs activate SREBP-regulated expression of lipid biosynthetic genes in cultured human glioma cells: a novel mechanism of action?", *The Pharmacogenomics Journal*, (2005) 5, 298-304.

Garyfallos, Case Report—"Olanzapine versus resperidone: weight gain and elevation of serum triglyceride levels", *European Psychiatry 18* (2003) 320-321; 2003 Editions scientifiques et medicales Elsevier SAS.

Georges et al., "Effect of Simvastatin on Desaturase Activities in Liver from Lean and Obese Zucker Rats", *LIPIDS*, vol. 28, No. 1 (1993), pp. 63-65.

German et al., "Metabolomics: building on a century of biochemistry to guide human health", *Metobolomics*, vol. 1. No. 1, Jan. 2005, pp. 3-9. DOI 10.1007/s11306-005-1102-8, Springer Science + Business Media, Inc.

German et al., *Symposium: Improving Human Nutrition through Genomics, Proteomics and Biotechnologies*, "Personal Metabolomics as a Next Generation Nutritional Assessment[1, 2]", *JN The Journal of Nutrition*, pp. 4260-4266. 2003 American Society for Nutritional Sciences.

Goodenowe et al., "Peripheral ethanolamine plasmalogen deficiency; a logical causative factor in Alzheimer's disease and dementia", *Journal of Lipid Research*, vol. 48, 2007, pp. 2485-2498.

Grundy et al., "Implications of Recent Clinical Trials for the National Cholesterol Education Program Adult Treatment Panel III Guidelines", *NCEP Report*, Downloaded from circ.ahajournals.org by on Mar. 14, 2011, DOI: 10.1161/01.CIR.0000133317.49796.0E, pp. 227-240.

Grundy et al., "United States Cholesterol Guidelines 2001: Expanded Scope of Intensive Low-Density Lipoprotein-Lowering Therapy", *Am J Cardiol*, 2001;88:23J-27.

Harris et al., "Statin treatment alters serum n-3 and n-6 fatty acids in hypercholesterolemic patients", *Prostaglandins, Leukotrienes and Essential Fatty Acids*, 71 (2004) 263-269.

Henderson, "Clozapine: Diabetes Mellitus, Weight Gain, and Lipid Abnormalities", *J Clin Psychiatry* 2001; 62 (suppl 23); From the Department of Psychiatry and the Schizophrenia Program, Massachusetts General Hospital and Harvard Medical School, Boston; Presented at the symposium "Effects of Drugs on Body Weight and Glucose Regulation", Dec. 16, 2000; New York University School of Medicine, New York; pp. 39-44.

Hennen et al., "Weight Gain During Treatment of Bipolar I Patients With Olanzapine", *J Clin Psychiatry* 2004; 65: 1679-1687; pp. 1679-1687.

Holmes et al., "Metabolic Profiling of CSF: Evidence That Early Intervention May Impact on Disease Progression and Outcome in Schizophrenia" *PLoS Medicine*, Aug. 2006, vol. 3, Issue 8, pp. 1420-1428.

Horrobin et al., "Essential Fatty Acids in Plasma Phospholipids in Schizophrenics" *Biol Psychiatry*, 1989;25:562-568.

Horrobin et al., "Fatty Acid Levels in the Brains of Schizophrenics and Normal Controls" *Biol Psychiatry* 1991:30:795-805.

Horrobin, "Schizophrenia as a membrane lipid disorder which is expressed throughout the body" *Prostaglandins, Leukotrienes and Essential Fatty Acids* (1996) 55(1&2), 3-7.

Horrobin, "The membrane phospholipid hypothesis as a biochemical basis for the neurodevelopmental concept of schizophrenia", *Schizophrenia Research* 30 (1998) 193-208.

Huang et al., "Serum lipid profiles and schizophrenia: Effects of conventional or atypical antipsychotic drugs in Taiwan", *Schizophrenia Research* 80 (2005) 55-59; doi: 10.1016/j.schres.2005.05001.

Isley et al., "The effect of high-dose simvastatin on triglyceride-rich lipoprotein metabolism in patients with type 2 diabetes mellitus", *Journal of Lipid Research*, vol. 47, 2006, pp. 193-200.

Jasinska et al., "Statins: a new insight into their mechanisms of action and consequent pleiotropic effects", *Pharmacological Reports*, 2007, 59, 483-499.

Jow et al., "Leptin and cholesterol levels are low in major depressive disorder, but high in Schizophrenia", *Journal of Affective Disorders* 90 (2006) 21-27; doi: 10.1016/j.jad.2005.09.015.

Jula et al., "Effects of Diet and Simvastatin on Fatty Acid Composition in Hypercholesterolemic Men", *Arterioscler Thromb Vasc Biol.* 2005;25:1952-1959.

Kaddurah-Daouk et al., "Metabolomic mapping of atypical antipsychotic effects in schizophrenia", *Molecular Psychiatry* (2007) 12, 934-945.

Kaddurah-Daouk et al., "Metabolomics: A Global Biochemical Approach to Drug Response and Disease", *Annu, Rev. Pharmacol, Toxicol.* 2008. 48:653-83.

Kaddurah-Daouk et al., "Metabolomics: A Global Biochemical Approach to the Study of Central Nervous System Diseases", *Neuropsychopharmacology REVIEWS* (2009) 34, 173-186.

Kaddurah-Daouk et al., "Metabolomics: A New Approach Towards Identifying Biomarkers and Therapeutic Targets in CNS Disorders", *Metabolic Profiling*, 2004,Chapter 4, pp. 45-63. G. Harrigan et al. (eds), Klower Academic Publishers.

Kaddurah-Daouk, "Metabolic Profiling of Patients with Schizophrenia", *PLoS Medicine*, Aug. 2006, vol. 3, Issue 8, e363, pp. 1222-1223, DOI: 10.1371/journal.pmed.0030363.

Kaiya et al., "Essential and Other Fatty Acids in Plasma in Schizophrenics and Normal Individuals from Japan" *Biol Psychiatry*, 1991;30:357-362.

Kenny et al., "Novel biomarkers for pre-eclampsia detected using metabolomics and machine learning" Metabolomics Vo. 1, No. 3, Jul. 2005, DOI: 10.1007/s11306-005-0003-1, pp. 227-234.

Keshavan et al., "Erythrocyte Membrane Phospholipids in Psychotic Patients" *Psychiatry Research*, 49:89-95, date unknown.

Kingsbury et al., "The Apparent Effects of Ziprasidone on Plasma Lipids and Glucose", *J Clin Psychiatry* 62:5, May 2001; pp. 347-349.

Kinon, et al., "Longitudinal Effect of Olanzapine on Fasting Serum Lipids", *Ann. N.Y. Acad. Sci.* 1032: 295-296 (2004); doi: 10.1196/annals.1314.043.

Kinon, et al., "Long-Term Olanzapine Treatment: Weight Change and Weight-Related Health Factors in Schizophrenia", *J Clin Psychiatry* 62:2, Feb. 2001; pp. 92-100.

Klein-Platat et al., "Plasma fatty acid composition is associated with the metabolic syndrome and low-grade inflammation in overweight adolescents", *Am J Clin Nutr*, 2005;82:1178-84.

Laaksonen et al., "A Systems Biology Strategy Reveals Biological Pathways and Plasma Biomarker Candidates for Potentially Toxic Statin-Induced Changes in Muscle", *PLoS One*, Dec. 2006, Issue 1, e97 (9 pages).

Lee et al., "Plasma Cholesteryl Esters Provided by Lecithin:Cholesterol Acyltransferase and Acyl-Coenzyme A:Cholesterol Acyltransferase 2 Have Opposite Atherosclerotic Potential", Downloaded from circres.ahajournals.org by on Mar. 14, 2011, DOI: 10.1161/01.RES.0000147558.15554.67, pp. 998-1018.

Levick et al., "Arachidonic Acid Metabolism as a Potential Mediator of Cardiac Fibrosis Associated with Inflammation", *The Journal of Immunology*, Downloaded from www.jimmunol.org on Mar. 14, 2011, pp. 641-646.

Lindon et al., Review: "Metabonomics technologies and their applications in physiological monitoring, drug safety assessment and disease diagnosis", *Biomarkers*, vol. 9, No. 1 (Jan.-Feb. 2004) pp. 1-31, Taylor & Francis Ltd.

Liu et al., "Specificity of lecithin:cholesterol acyltransferase and atherogenic risk: comparative studies on the plasma composition and in vitro synthesis of cholesteryl esters in 14 vertebrate species", *Journal of Lipid Research*, vol. 36, 1995, pp. 1813-1824.

Ma et al., "Relation of plasma phospholipid and cholesterol ester fatty acid composition to carotid artery intima-media thickness:the Atherosclerosis Risk in Communities (ARIC) Study", *Am J Clin Nutr*, 1997;65:551-9.

Mahadik et al., "Plasma membrane phospholipid and cholesterol distribution of skin fibroblasts from drug-naïve patients at the onset of psychosis", *Schizophrenia Research* 13 (1994) 239-247.

Mahakik et al., "Phospholipids in Schizophrenia", *Textbook of Schizophrenia*, 2006, Chapter 7, pp. 117-135, Lieberman JA et al. (eds), American Psychiatric Publishing, Washington, D.C.

McQuade et al., A Comparison of Weight Change During Treatment With Olanzapine or Aripiprazole: Results From a Randomized, Double-Blind Study, *J Clin Psychiatry* 2004; 65 (suppl 18) pp. 47-56, Physicians Postgraduate Press, Inc.

Melkersson et al., "Relationship between levels of insulin or triglycerides and serum concentrations of the atypical antipsychotics clozapine and olanzapine in patients on treatment with therapeutic doses", *Psychopharmacology* (2003) 170:157-166; DOI 10.1007/s00213-003-1529-4.

Messner et al., "Fatty Acid Composition in Serum Among Males 4-16 Years After Myocardial Infarction", *International Journal of Circumpolar Health*, Original Research 57/1998, pp. 22-31.

Moilanen et al., "Fatty Acid Composition of Serum Cholesteryl Esters in Relation to Serum Lipids and Apolipoproteins in 3-18-year-old Finnish Children and Adolescents", *Atherosclerosis*, 59 (1986) 113-119, Elsevier Scientific Publishers Ireland, Ltd.

Neidlinger et al., "Hydrolysis of Phosphatidylserine-exposing Red Blood Cells by Secretory Phospholipase $A_2$ Generates Lysophosphatidic Acid and Results in Vascular Dysfunction", *The Journal of Biological Chemistry*, vol. 281, No. 2, pp. 775-781, Jan. 13, 2006.

Odunsi et al., "Detection of epithelial ovarian cancer using H-NMR-based metabonomics", *International Journal of Cancer*, vol. 113, Issue 5, pp. 782-788, Feb. 20, 2006.

Ozerova et al., "Effects of Simvastatin on the Phospholipid Composition of High-Density Lipoproteins in Patients with Hypercholesterolemia", *Bulletin of Experimental Biology and Medicine*, No. 2, 2001 Biophysics and Biochemistry, pp. 763-765.

Pettegrew et al., "Alterations in Brain High-Energy Phosphate and Membrane Phospholipid Metabolism in First-Episode, Drug-Naïve Schizophrenics" *Arch Gen Psychiatry*—vol. 48, Jun. 1991, pp. 563-568.

Prabakaran et al., "Mitochondrial dysfunction in schizophrenia: evidence for compromised brain metabolism and oxidative stress", *Molecular Psychiatry* (2004) 9, 684-697, Nature Publishing Group.

Quinones et al., "Metabolomics tools for identifying biomarkers for neuropsychiatric diseases", *Neurobiology of Disease* 35 (2009) 165-176.

Raeder et al., "Antidepressant drugs activate SREBP and up-regulate cholesterol and fatty acid biosynthesis in human glial cells", *Neuroscience Letters*, 395 (2006) 185-190.

Ridker et al., "Rosuvastatin to Prevent Vascular Events in Men and Women with Elevated C-Reactive Protein", *The New England Journal of Medicine*, Nov. 20, 2008, vol. 359, No. 21, pp. 2195-2207.

Riséet al., "Δ5 desaturase mRNA levels are increased by simvastatin via SREBP-1 at early stages, not via PPARα, in THP-1 cells", *European Journal of Pharmacology* 571 (2007) 97-105.

Riséet al., "Relative potencies of statins in reducing cholesterol synthesis and enhancing linoleic acid metabolism", *European Journal of Pharmacology* 467 (2003) 73-75.

Riséet al., "Statins enhance arachidonic acid synthesis in hypercholesterolemic patients", *Nutr Metab Cardiovasc Dis* (2001) 11:88-94.

Risérus, "Rosiglitazone Increases Indexes of Stearoyl-CoA Desaturase Activity in Humans", *Diabetes*, vol. 54, May 2005, pp. 1379-1384, the American Diabetes Association.

Rotrosen et al., "Phospholipid and Prostaglandin Hypotheses of Schizophrenia", 1987, Chapter 74, pp. 759-764, edited by Herbert Y. Meltzer, Raven Press New York.

Rozen et al., "Metabolomic analysis and signatures in motor neuron disease", *Metabolomics* vol. 1, No. 2, Apr. 2005 DOI: 10.1007/s11306-005-4810-1, pp. 101-108.

Schmitt et al., "Effects of antipsychotic treatment on membrane phospholipid metabolism in schizophrenia" *J Neural Transm* (2001) 108:1081-1091.

Shiwaku et al., "Triglyceride levels are ethnic-specifically associated with an index of stearoyl-CoA desaturase activity and n-3 PUFA levels in Asians", *Journal of Lipid Research*, vol. 45, 2004, pp. 914-922.

Simon et al., "Phenotypic Predictors of Response to Simvastatin Therapy Among African-Americans and Caucasians: The Cholesterol and Pharmacogenetics (CAP) Study", *Am J Cardiol* 2006;97:843-850.

Sotiriou et al., "Beneficial Effects of Statins in Coronary Artery Disease—Beyond Lowering Cholesterol", *The Annals of Pharmacotherapy*, Dec. 2000, vol. 34, pp. 1432-1439.

Sunstrom et al., "Dyslipidemia and an Unfavorable Fatty Acid Profile Predict Left Ventricular Hypertrophy 20 Years Later", Downloaded from www.circ.ahajournals.org by on Mar. 14, 2011, pp. 836-841.

Wang et al., "Plasma Phospholipid Metabolic Profiling and Biomarkers of Type 2 Diabetes Mellitus Based on High-Performance Liquid Chromatography/Electrospray Mass Spectrometry and Multivariate Statistical Analysis" *Analytical Chemistry*, vol. 77, No. 13, Jul. 1, 2005 (pp. 4105-4116).

Warensjo et al., "Fatty acid composition and estimated desaturase activities are associated with obesity and lifestyle variables in men and women" *Nutrition, Metabolism & Cardiovascular Diseases* (2006) 16, 128-136.

Watkins et al. "Lipid metabolome-wide effects of the PPARγ agonis rosiglitazone" *Journal of Lipid Research*, vol. 43, 2002, pp. 1809-1817.

Watkins et al., "Metabolomics and biochemical profiling in drug discovery and development", *Current Opinion in Molecular Therapeutics* (2002) 4(3):224-228 @ PharmaPress Ltd ISSN 1464-8431.

Watkins, "Lipomic profiling in drug discovery, development and clinical trial evaluation", *Current Opinion in Drug Discovery & Development*, 2004 7(1):112-117, Thomson Scientific ISSN 1367-6733.

Watson et al., "Lipidomics: A Global Approach to Lipid Analysis in Biological Systems", *Journal of Research ASBMB*, Downloaded from www.jlr.org at Duke Medical Library, on Feb. 15, 2011, pp. 1-47.

Yanagita et al., "Effects of Simvastatin, a Cholesterol Synthesis Inhibitor, on Phosphatidylcholine Synthesis in HepG$_2$ Cells," *Clinical Therapeutics*, vol. 16, No. 2 (1994), pp. 200-208.

Yao et al., "Correlations between Peripheral Polyunsaturated Fatty Acid Content and in Vivo Membrane Phospholipid Metabolites", *Biol Psychiatry* 2002;52:823-830.

Yao et al., "Membrane phospholipid abnormalities in postmortem brains from schizophrenic patients", *Schizophrenia Research* 42 (2000) 7-17.

Yao et al., "Metabolic Investigation in Psychiatric Disorders", *Molecular Neurobiology*, vol. 31, 2004, pp. 193-203.

Yao et al., "Red blood cell membrane dynamics in schizophrenia. II. Fatty acid composition", *Schizophrenia Research*, 13 (1994) 217-226.

* cited by examiner

LIPIDOMIC APPROACHES TO DETERMINING DRUG RESPONSE PHENOTYPES IN CARDIOVASCULAR DISEASE

RELATED APPLICATION INFORMATION

This application claims priority from U.S. Provisional Application Ser. No. 60/985,805, filed Nov. 6, 2007, the disclosure of which is incorporated by reference in its entirety, and International Application No. PCT/US2007/009916, filed Apr. 24, 2007, which claims priority from U.S. Provisional Application Ser. No. 60/794,807, filed Apr. 24, 2006, the disclosures of which are incorporated by reference in their entireties.

STATEMENT OF GOVERNMENT SUPPORT

This invention was made, in part, with government support under grant number GM-078233 from the National Institute of General Medical Sciences of the National Institutes of Health and under grant number U01 HL069757 from the National Institutes of Health. The United States government has certain rights to this invention.

FIELD OF THE INVENTION

The present invention relates to lipidomics; in particular, the present invention relates to the application of lipidomics to evaluate statin treatment for disorders such as cardiovascular disorders.

BACKGROUND OF THE INVENTION

Statins, the HMG CoA reductase inhibitors, are lipid lowering drugs used to treat cardiovascular disease (CVD), a disease that affects over 64 million Americans and remains the leading cause of death in both sexes and for all major ethnic groups in the U.S. Statins act to reduce blood cholesterol levels by the inhibition of HMG CoA reductase and are the largest single class of drugs prescribed for CVD prevention, with over 120 million prescriptions in 2003. The primary clinical rationale for the use of statins is to reduce the level of LDL-cholesterol and, thereby, to reduce CVD risk. This effect is due in large part to increased LDL and IDL clearance as a result of the up regulation of LDL receptors. Multiple intervention trials with statin drugs have demonstrated a remarkable degree of consistency in their ability to reduce risk for both CVD and stroke by an average of approximately ¼ to ⅓. Moreover, in studies such as the landmark Heart Protection Study, similar benefit has been observed among multiple population subgroups, including men and women, older vs. younger individuals, diabetic vs. nondiabetic subjects, and individuals with a range of baseline CVD risk factors, including elevations in LDL cholesterol as well as other lipids and lipoproteins. Nevertheless, in all of these trials, residual CVD risk remains high (60-75%), and potential drug-related toxicity, while infrequent, is a significant concern, i.e., there is large individual variation in the drug response phenotype after statin therapy.

Several studies, including the Cholesterol/Atherosclerosis Pharmacogenetics (CAP) study have demonstrated a wide range of lipid and lipoprotein responses to statin therapy (J. Simon et al., Phenotypic Predictors of Response to Simvastatin Therapy Among African-Americans and Caucasians: The Cholesterol and Pharmacogenetics (CAP) Study, *Am. J. Cardiol.* 2006; 97: 843-850). The decrease in LDL cholesterol for a given statin in apparently similar individuals has been found to range from less than 5% to greater than 60%, even when compliance is taken into account. Similar variation has been observed for other statin effects that can contribute to CVD outcomes, including reductions in triglyceride and VLDL, increases in HDL, and reductions in C-reactive protein. Mechanisms for the observed drug response phenotypes remain illusive.

Statin therapy provides outcome benefit to only about 30% of treated individuals (LaRosa et al. JAMA 1999; 282:2340-6). Although statins appear reasonably benign from a safety perspective (with a few notable exceptions), the decision to treat involves some risk (e.g., rhabdomyolysis) and considerable expense to both individuals and to payers. Thus, effective tools for predicting those individuals who will respond to statin therapy would provide benefit to both individuals and the healthcare system. However, because statins are relatively safe and because outcome can be measured from a cholesterol reduction after several weeks of therapy, an effective test should be both accurate and predictive of response shortly after commencing therapy or even from a pre-treatment sample.

The present invention provides methods for predicting responsiveness to statin therapy based on lipidomic analysis.

SUMMARY OF THE INVENTION

While statins are effective cholesterol lowering agents, there is a very large inter-personal variation in the response to statin therapy. Part of the variability in response is genetic, but other factors may play a role such as biochemical variation among individuals. As discussed further below, a specialized metabolomics platform referred to as "lipidomics" was used that quantifies hundreds of lipid metabolites (across multiple lipid classes) to evaluate global lipid changes resulting from statin treatment. Metabolic changes were evaluated in "good" and "poor" responders with response being defined as percentage change in LDL cholesterol after treatment to define biochemical pathways that might be regulated differently between the two groups and to define a set of biomarkers that correlate with response. Samples were selected from studies conducted by the Pharmacogenetics and Risk of Cardiovascular Disease (PARC) Study Group where 944 African-American and white men and women completed an open-label, 6-week pharmacogenetics trial with 40 mg of simvastatin.

As discussed below, a group of 24 "good" responders was selected from the top 10% of responders in the CAP study and matched for age, gender, and ethnic background to 24 subjects in the lowest 10% of responders. The study was done as two sets (24 each) allowing for replication of findings. Significant lipid changes are highlighted in responders suggesting that the drug targets several lipid pathways in this group of individuals. Far fewer lipid changes were noted in non-responders. Differences in lipid metabolites between responders and non-responders were identified that point to lipid biochemical pathways that are differently regulated between the two groups and that result in a set of biomarkers that correlate with statin response.

There have been reports concerning the application of metabolomic techniques for drug discovery, disease treatment, and diagnosis that have mentioned CVD, but have neither described nor suggested their application to statin treatment regimens. See, e.g., U.S. Pat. No. 7,005,255 (R. Kaddurah-Daouk and B. Kristal.)

Previous investigations into statin pharmacology have identified the activation of the delta-5 desaturase as a response to treatment. In these studies, investigators have noted increased arachidonic acid (20:4 n6) and other delta-5 desaturase products. However, in all cases the studies reported changes in total serum fatty acid composition, not changes in individual lipid class compositions (as reported herein). Further, none of these studies differentiated between good and poor responders or suggested methods of using metabolic signatures as predictive and/or response markers to identify those subjects who will have a positive response to statin treatment.

The identification of drug activity biomarkers that stratify individuals based on likely response to the particular therapeutic, both positive response, efficacy, and negative response, development of side effect or toxicity would be advantageous for fulfilling the promise of individualized therapeutic interventions. The present invention provides new approaches for identifying biomarkers that define drug response phenotypes for statin drugs used to prevent and/or treat cardiovascular disease.

Accordingly, a first aspect of the invention is a method of correlating a lipid profile with a positive or negative response to a statin treatment regimen, the method comprising: obtaining a lipid profile of a sample from a mammalian subject following commencement of the treatment regimen; and correlating the lipid profile in the sample with a positive or negative response to the treatment regimen.

A further aspect of the invention is a method of correlating a lipid profile with a positive or negative response to a statin treatment regimen, the method comprising: obtaining a lipid profile of a sample from a mammalian subject before commencement of the treatment regimen; and correlating the lipid profile in the sample with a positive or negative response to the treatment regimen.

A still further aspect of the invention is the use of a means of detecting a lipid profile in a biological sample of a subject in determining if the subject is responding or will respond positively or negatively to a statin treatment regimen (see, e.g., A. Roses et al., EP 0 625 212 B1).

These and other aspects of the invention are set forth in more detail in the following description of the invention.

DETAILED DESCRIPTION OF THE INVENTION

Figure 1:
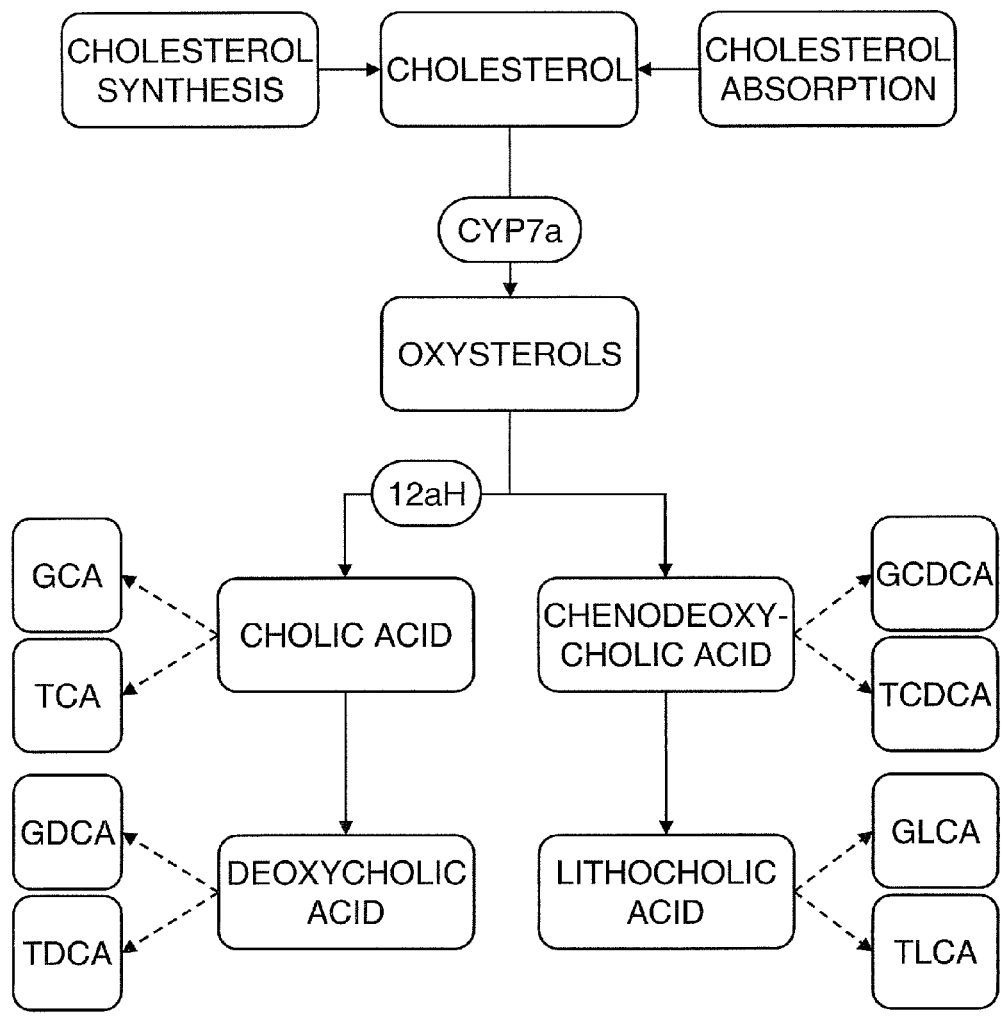
FIG. 1. Cholesterol metabolism and homeostasis in humans. Metabolites comprising these pathways are listed in Table 10. Cholesterol synthesis can be assessed by measuring the concentrations of endogenous sterols. Cholesterol absorption can be assessed by measuring the concentrations of phytosterols and bile acid conjugates. Cholesterol excretion as bile can be assessed by measuring the concentrations of oxysterols, bile acids and bile acid conjugates. Abbreviations: "CYP7a", cholesterol 7α hydroxylase.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

The terminology used in the description of the invention herein is for the purpose of describing particular embodiments only and is not intended to be limiting of the invention.

As used herein, the singular forms "a," "an" and "the" are intended to include the plural forms as well, unless the context clearly indicates otherwise.

As used herein, "and/or" refers to and encompasses any and all possible combinations of one or more of the associated listed items.

Moreover, the present invention also contemplates that in some embodiments of the invention, any feature or combination of features specifically set forth herein can be excluded or omitted.

Those skilled in the art will appreciate that all of the methods of the invention of the present invention can be practiced with any combination of the features described herein, including but not limited to: subject, sample, CVD, and component(s) of the lipid profile, the latter including without limitation the classes and subclasses of lipids evaluated in the profile, and the manner in which they are evaluated (e.g., methodology used and method of expressing the results [for example, as an absolute amount such as weight or moles or a relative amount such as a weight %, mole % or ratio]).

Further, any feature of the invention that is specifically described herein can be included or omitted from the invention (e.g., can be disclaimed).

The following abbreviations are used herein:

| Lipid Metabolite | Abbreviation |
| --- | --- |
| Cholesterol Ester | CE |
| Diacylglycerol | DG |
| Plasmalogen linked fatty acids | dm |
| Free fatty acid | FA |
| Free cholesterol | FC |
| Total lipid class | LC |
| Lysophosphatidylcholine | LY |
| Lysophosphatidylcholine | LYPC |
| Monoacylglycerol | MAG |
| Mono unsaturated fatty acid | MUFA |
| Phosphatidic acid | PA |
| Phosphatidylcholine | PC |
| Phosphatidylethanolamine | PE |
| Phosphatidylglycerol | PG |
| Phosphatidylinositol | PI |
| Phospholipids | PL |
| Phosphatidylserine | PS |
| Polyunsaturated fatty acid | PUFA |
| Saturated fatty acid | SFA |
| Trans | t |
| Triacylglycerol | TG |
| Fatty acids with n3 double bonds | n3 |
| Fatty acids with n6 double bonds | n6 |
| Fatty acids with n7 double bonds | n7 |
| Fatty acids with n9 double bonds | n9 |
| Cholesterol | CHOL |
| Lanosterol | LANO |
| Lathosterol | LATH |
| Cholestanol | CSTN |
| 7-dehydrocholesterol | 7-DHC |
| β-Sitosterol | β-SITO |
| Campesterol | CAMP |
| Desmosterol | DESM |
| Stigmasterol | STIG |
| 7α-hydroxycholesterol | 7α-HC |
| 4-cholesten-7α-ol-3-one | 4-CHST |
| Cholic acid | CA |
| Chenodeoxycholic acid | CDCA |
| Deoxycholic acid | DCA |
| Lithocholic acid | LCA |
| Ursodeoxycholic acid | UDCA |
| Glycocholic acid | GCA |
| Taurocholic acid | TCA |
| Glycodeoxycholic acid | GDCA |

-continued

| Lipid Metabolite | Abbreviation |
| --- | --- |
| Taurodeoxycholic acid | TDCA |
| Glycodeoxycholic acid | GDCA |
| Taurodeoxycholic acid | TDCA |
| Glycolithocholic acid | GLCA |
| Taurolithocholic acid | TLCA |
| Glycoursodeoxycholic acid | GUDCA |
| Zymosterol | ZYMO |
| Coprostanol | COPR |
| Glycochenodeoxycholic acid | GCDCA |
| Taurochenodeoxycholic acid | TCDCA |
| Ursodeoxycholic acid | UDCA |

Phospholipids are formed from four components: a backbone to which is linked two fatty acid-derived "tails" by ester linkages and one "head" group by a phosphate ester, and an alcohol. Phospholipids with a glycerol backbone are known as glycerophospholipids or phosphoglycerides. Sphingomyelin is a phospholipid with a sphingosine backbone. Phospholipids are a major component of all biological membranes, along with glycolipids and cholesterol. The head groups of the phospholipids found in biological membranes are phosphatidylcholine (lecithin), lysophosphatidyl choline, phosphatidylethanolamine, phosphatidylserine and phosphatidylinositol, whose head group can be modified by the addition of one to three more phosphate groups. While phospholipids are the major component of biological membranes, other lipid components like sphingolipids and sterols (such as cholesterol in animal cell membranes) are also found in biological membranes.

Cardiolipin (diphosphatidyl glycerol) is an important component of the mitochondrial membrane, typically present in metabolically active cells of the heart and skeletal muscle. It has also been observed in certain bacterial membranes. It serves as an insulator and stabilizes the activity of protein complexes important to the electron transport chain.

Fatty acids are unbranched hydrocarbon chains, connected by single bonds alone (saturated fatty acids) or by both single and double bonds (unsaturated fatty acids). Examples of saturated fatty acids include but are not limited to butyric acid, lauric acid, myristic acid, pentadecanoic acid, palmitic acid, stearic acid, arachidic acid, behenic acid and lignoceric acid. Examples of unsaturated fatty acids include but are not limited to linolenic acid, docosahexaenoic acid, eicosapentaenoic acid, linoleic acid, arachidonic acid, oleic acid, and erucic acid. Particular classes of fatty acids include omega-3 fatty acids (e.g., alpha-linolenic, stearidonic, eicosatrienoic, eicosatetraenoic, eicosapentaenoic, docosapentaenoic, docosahexaenoic and tetracosahexaenoic acids), omega-6 fatty acids (e.g., linoleic, gamma-linolenic, eicosadienoic, homo-gamma-linolenic, arachidonic, docosadienoic, docosatetraenoic and 4,7,10,13,16-docosapentaenoic acids) and omega-9 fatty acids (e.g., myristoleic, palmitoleic, vaccenic, oleic, eicosenoic, mead, erucic and nervonic acids). Other fatty acids include plasmalogen-linked fatty acids including but not limited to plasmalogen 16:0, plasmalogen 18:0, plasmalogen 18:1n7 and plasmalogen 18:1n9. Other fatty acids include but are not limited to palmitelaidic acid, elaidic acid, 8-eicosaenoic acid and 5-eicosaenoic acid.

Essential fatty acids include the polyunsaturated fatty acids, linoleic acid and alpha-linolenic acid, which are the parent compounds of the omega-6 and omega-3 fatty acid series, respectively. They are essential in the human diet since they cannot be synthesized by the body, as the enzymes to introduce a double bond at the omega-3 and omega-6 positions are absent. The essential fatty acids are important for the immune system and in blood pressure regulation, since they are used to make compounds such as prostaglandins. The brain is also highly enriched in derivatives of linolenic and linoleic acids.

The foregoing discussion applies to free fatty acids and to fatty acid moieties found incorporated into lipid molecules in other classes (e.g., diglycerides, triglycerides and phospholipids).

Triglycerides (triacylglycerols) are the most abundant dietary lipids. They are the form in which reduced carbon is stored for energy. Each triacylglycerol has a glycerol backbone to which 3 fatty acids are esterified. Most triacylglycerols are "mixed" in that the three fatty acids differ in chain length and/or number of double bonds.

Sterols (sometimes called steroid alcohols) are steroids with a hydroxyl group at the 3-position of the A-ring (see, e.g., Subramaniam et al. A comprehensive classification system for lipids. *J. Lipid Res.* 464: 839-61). Sterols are amphipathic lipids synthesized from acetyl-coA via the HMG-COA reductase pathway. The hydroxyl group on the A ring is polar, whereas the rest of the aliphatic chain is non-polar. Plant sterols are called "phytosterols" (e.g., campesterol, sitosterol, stigmasterol) and sterols of animal origin are called "endogenous sterols" or sometimes "zoosterols" (e.g., cholesterol and some steroid hormones). In particular embodiments of the present invention, endogenous sterols can be evaluated as markers of cholesterol biosynthesis. Further, in embodiments of the invention, phytosterols are indicative of cholesterol absorption.

Oxysterols are oxidized derivatives of sterols and include without limitation 7α-OH-cholesterol, 7β-OH-cholesterol, (24S)-24-OH-cholesterol, (25R)-26-OH-cholesterol, 7-keto-cholesterol, 25-OH-cholesterol, 5α,6α-epoxy-cholesterol, 5β,6β-epoxy-cholesterol, 5α,6β-diOH-cholesterol, 26-hydroxycholestanol, cholest-4-ene-3β,26-diol, and cholest-4-ene-3β,6-diol. In embodiments of the invention, oxysterols are indicative of cholesterol degradation.

Bile acids, which are also known as bile salts, are steroid acids. Bile acids are produced in the liver by the oxidation of cholesterol and represent degradation products of cholesterol. In humans, the rate-limiting step in the production of bile acids is the addition of a hydroxyl group on the 7 position of the steroid nucleus by the enzyme cholesterol 7α-hydroxylase. The term "bile acid" refers to the conjugated form. In the alkaline environment of the intestine, the bile acids are converted to "bile salts," which are the ionic form of the secreted bile acid. About half of the body's cholesterol is converted to bile acids, and about 20-30 grams of bile acids are secreted into the intestine daily. However, about 90% of excreted bile acids are reabsorbed in the ileum and recycled by the process of enterohepatic circulation. Bile acids produced by the mammalian liver are called "primary bile acids," whereas those produced by the intestinal microflora as a result of chemical modification of bile acids produced by the mammalian host are termed "secondary bile acids." Nonlimiting examples of primary bile acids include cholic acid, chenodeoxycholic acid, glycocholic acid, glycochenodeoxycholic acid, glycoursodeoxycholic acid, taurocholic acid, and taurochenodeoxycholic acid. Nonlimiting examples of secondary bile acids include lithocholic acid, deoxycholic acid, ursodeoxycholic acid, glycodeoxycholic acid, glycolithocholic acid, taurodeoxycholic acid, taurolithocholic acid, deoxycholic acid, taurodeoxycholic acid and glycodeoxycholic acid. In general, increases in bile acids can indicate increased cholesterol degradation.

Bile acid conjugates are formed between bile acids and an amino acid such as glycine or taurine.

Unless indicated otherwise, as used herein, the term "bile acid" or "bile acids" includes bile salts and bile acid conjugates.

In some instances, lipid metabolites are identified herein by the lipid class and, if relevant, the fatty acid moiety. In the context of this invention, fatty acids are identified first by the number of carbons in the molecule (e.g., 20), the number of double bonds in the molecule (e.g., 4), and lastly the position of the double bonds (e.g., n6). To illustrate, PC20:4n6 denotes a phosphatidylcholine molecule containing a 20 carbon fatty acid with 4 double bonds at the n6 position.

A "lipid metabolite" as used herein can refer to a single species within a lipid class (e.g., PC20:4n6), a subset of species within a lipid class (e.g., PCn6 or PCMUFA) or the entire lipid class (e.g., Total PE).

"Treatment regimen" as used herein that may be for the treatment of any disorder for which statins are administered, including but not limited to cardiovascular disease. In general such treatment regimens involve the regular (e.g., daily, every other day) administration (e.g., oral administration) of an active agent over an extended period of time (e.g., at least two weeks, and generally at least one or two months). In some embodiments the treatment regimen is an HMGCoA reductase inhibitor or statin treatment regimen, including but not limited to simvastatin treatment regimens.

"HMGCoA reductase inhibitors" include, but are not limited to, statins such as cerivastatin, atorvastatin, simvastatin, mevastatin, pravastatin, fluvastatin, lovastatin, rosuvastatin, pitavastatin, itavastatin, ZD4522, etc. See, e.g., U.S. Pat. Nos. 7,166,578 and 7,186,746.

The lipidomic profiles of the invention are correlated with "positive" or "negative" responses to statin treatment. A "positive" or "good" response (and similar terms) or, conversely, a "negative" or "poor" response (and similar terms) to statin treatment can be with reference to any clinical measure known in the art, e.g., a change in LDL cholesterol level, total cholesterol level, total triglycerides and/or HDL cholesterol. For example, a positive response to statin treatment can be defined as a reduction in LDL cholesterol, total cholesterol, and/or total triglyceride level. In representative embodiments, the lipidomic approaches of the invention can predict whether a subject will have a positive or negative response to statin treatment prior to commencing the treatment. In other exemplary embodiments, the lipidomic profiling will indicate whether a subject is having a positive or negative response to the statin treatment regimen at a time point prior to when improvement in clinical indicia would be detected (e.g., LDL cholesterol).

"Cardiovascular disease" (also referred to as "cardiovascular disorder" herein) as used herein may be any type, or characterized by any measure, of cardiovascular disease, including but not limited to restenosis, cardiomegaly, atherosclerosis, myocardial infraction, congestive heart failure, hypercholesterolemia (including hyperLDL-cholesterolemia), hypertriglyceridemia, angina pectoris, coronary artery disease (or coronary heart disease), hypertension, stroke, myocardial ischemia, arrhythmia, low grade vascular inflammation, peripheral vascular disease, peripheral arterial disease, an acute vascular syndrome, a microvascular disease (such as nephropathy, neuropathy, retinopathy and nephrotic syndrome, and the like).

"Active agents" that can be administered in combination with statins in a statin treatment regimen include, but are not limited to, beta adrenergic blockers, calcium channel blockers, ACE inhibitors, angiotensin II receptor antagonists, antithrombotics, HMGCoA reductase inhibitors, aspirin, calcium channel blockers, diuretics, etc., See, e.g., U.S. Pat. No. 7,169,805

The term "lipidomics" as used herein refers to the use of metabolomics as applied to the evaluation of lipid metabolites in biological samples. Lipid profiling generally involves an evaluation of lipid metabolites in one or more lipid classes (e.g., fatty acids, triglycerides, diglycerides, cholesterol esters, the phospholipid classes (including phosphatidylcholine, phosphatidylethanolamine, lysophosphatidylcholine, sphingomyelin, phosphatidylserine, phosphatidylethanolamine, cardiolipin), sterols, phytosterols, endogenous sterols, oxysterols, bile acids, primary bile acids and/or secondary bile acids.

As used herein, the term "lipid" is intended broadly and encompasses a diverse range of molecules that are relatively water-insoluble or nonpolar compounds of biological origin, including waxes, triglycerides, free fatty acids, diacylglyercols, fatty-acid derived phospholipids, sphingolipids, glycolipids and terpenoids, such as retinoids, cholesterol, cholesterol esters, steroids, etc. Some lipids are linear aliphatic molecules, while others have ring structures. Some are aromatic, while others are not.

As used herein, the term lipid "class" refers to a collection of lipid molecules that share structural and/or biochemical properties. According to the methods of the invention, lipids within any class(es) can be evaluated. Suitable lipid classes include polar and non-polar classes of lipids. Exemplary non-polar lipid classes include without limitation the free fatty acids, monoacylglycerides, diacylglycerides, triacylglycerides, sterols, and/or cholesterol esters. Exemplary polar classes include without limitation the phospholipid classes such as phosphatidic acid, lysophosphatidylcholine, sphingomyelin, phosphatidylinositol, phosphatidylglycerol, phosphatidylcholine, phosphatidylserine, phosphatidylethanolamine, lysophosphatidylethalolamine, cardiolipin, and/or lysocardiolipin. Other lipid classes include without limitation sterols, phytosterols, endogenous sterols, oxysterols, bile acids, primary bile acids and/or secondary bile acids.

The term "lipid profile" as used herein refers to the evaluation of one or more lipid metabolites within a biological sample. In particular embodiments, two or more, three or more, four or more, five or more, six or more, seven or more, eight or more, nine or more, ten or more, twelve or more, fifteen or more, twenty or more, fifty or more, 100 or more, or an even greater number of lipid metabolites are evaluated. In embodiments wherein two or more lipid metabolites are assessed, the two or more lipid metabolites can belong to the same class or can be belong to two or more, three or more, four or more, five or more, six or more, seven or more or a greater number of different lipid classes. For example, in representative embodiments, the lipid profile comprises lipid metabolites belonging to the sterol, bile acid and fatty acid classes.

The lipid profile can be quantitative, semi-quantitative and/or qualitative. For example, the lipid profile can evaluate the presence or absence of a lipid metabolite(s), can evaluate the presence of a lipid metabolite(s) above or below a particular threshold, and/or can evaluate the relative or absolute amount of a lipid metabolite(s). In particular embodiments, a ratio among two, three, four or more lipid metabolites is determined. Changes or perturbations in ratios of lipid metabolites can be advantageous in indicating where there are metabolic blocks (or releases of such blocks) or other alterations in metabolic pathways associated with disease, response to treatment, development of side effects, and the like (Methods of evaluating ratios of lipid precursors and products to evaluate enzyme activities and flow through metabolic pathways are known in the art (see, e.g., Attie et al., (2002) *J. Lipid Res.* 43:1899-1907 and Pan et al., (1995) *J. Clin. Invest.* 96:2802-2808).

Ratios of lipid metabolites can be used to reflect or assess changes in lipid metabolism. Generally, if the ratio is calculated from metabolites not present in the same lipid class, quantitative data are used to calculate the ratio. If the lipid metabolites reflected in the numerator and the denominator belong to the same lipid class, then relational data can be used.

In some embodiments, the level of a lipid metabolite is normalized against another lipid metabolite. For example, the ratio between two or more lipid metabolites can be normalized against an index associated with a pathway, enzymatic activity, class of metabolites, and/or status of certain metabolic activities. Alternatively the level of a lipid metabolite can be normalized against a housekeeping lipid metabolite, e.g., a lipid metabolite that is relatively stable in amount under a variety of conditions in the subject. In other embodiments, the level of a lipid metabolite is normalized against a non-housekeeping metabolite.

Quantitative metabolomic data include molar quantitative data, mass quantitative data and relational data by either moles or mass (mole % or weight %, respectively) for individual lipid metabolites or subsets of metabolites. In some embodiments, quantitative aspects of lipidomic analysis can be provided and/or improved by including one or more quantitative internal standards during the analysis, for instance, one standard for each lipid class. Internal standards are described in more detail in U.S. Patent Publication Nos. 2007/0032969 (T. H. Barrett et al.); 2006/0088860 (S. M. Watkins and M. W. Wiest); 2005/0009005 (S. M. Watkins); 2004/01434612 A1 (S. M. Watkins).

Truly quantitative data can be integrated from multiple sources (e.g., the data do not need to be generated with the same assay, in the same location and/or at the same time) into a single seamless database regardless of the number of metabolites measured in each, discrete, individual analysis.

A "change" in the level, amount, concentration, ratio and the like with respect to a lipid metabolite(s) can mean an increase or a decrease.

As used herein the term "level" is intended broadly and can mean a quantitative amount (e.g., weight or moles), a semi-quantitative amount, a relative amount (e.g., weight % or mole % within class or a ratio), a concentration, and the like.

In representative embodiments, the lipid profile provides a compositional analysis in which two or more, three or more, four or more, five or more, six or more, seven or more, eight or more, nine or more, ten or more, twelve or more, fifteen or more, twenty or more, fifty or more, one-hundred or more or a greater number of lipid metabolites are evaluated within a single class or within two or more, three or more, four or more, five or more, six or more, seven or more or a greater number of different lipid classes. Further, the lipid profile can assess two or more, three or more, four or more, five or more, six or more, seven or more or a greater number of different classes, and can evaluate two or more, three or more, four or more, five or more, six or more, seven or more, eight or more, nine or more, ten or more, twelve or more, fifteen or more, twenty or more, fifty or more, one-hundred or more or a greater number of lipid metabolites within each class. Optionally, the lipid profile provides a compositional analysis (e.g., mole percentage (%) of the lipid metabolite) within its class. For example, the lipid profile can include an evaluation (e.g., quantitation or determination of mole % within class) of two or more, three or more, four or more, five or more, six or more, seven or more, eight or more, nine or more, ten or more, twelve or more, fifteen or more, twenty or more, or a greater number of fatty acid moieties within one or more lipid classes (for example, diglyceride, triglyceride, phospholipid [e.g., lysophosphatidylcholine, sphingomyelin, phosphatidylcholine, phosphatidylserine, phosphatidylethanolamine, cardiolipin classes], sterol, endogenous sterol, phytosterol, oxysterol, bile acid, primary bile acid, and/or secondary bile acid classes).

The lipid profile can be based on measurements of individual metabolites, ratios between two or more metabolites, or a combination of both.

Analysis of the fatty acid class or fatty acid moieties incorporated into lipids of other classes can evaluate any characteristic including but not limited to chain length, the degree of saturation/desaturation and/or the position of any double-bond(s) that are present. With respect to chain length, the lipid profile can evaluate the presence of short- (e.g., 4 to 6 carbons), medium- (e.g., 6 to 10 carbons), long- (e.g., 12 to 18 carbons) and very long- (e.g., 20, 22 or more carbons) fatty acids, optionally with a further evaluation of saturation/desaturation. For example, in some embodiments saturated fatty acids are detected. In other embodiments, mono- and/or poly- (i.e., two or more unsaturated bonds) unsaturated fatty acids are evaluated. The position of the unsaturated bond(s) can also be evaluated, for example, omega-3 (i.e., n3), omega-6 (i.e., n6) and/or omega-9 (i.e., n9) fatty acids have double-bonds in the 3, 6 or 9 position, respectively. Further, the presence of cis or trans bonds within unsaturated fatty acids can be assessed.

Those skilled in the art will appreciate that the lipid profile can evaluate any combination of the foregoing characteristics of fatty acids (e.g., ratios, chain length, saturation/desaturation and/or position of any double-bonds), whether present in free fatty acids or fatty acid moieties incorporated into larger lipid molecules in other lipid classes.

It is intended that the lipid profile can evaluate free fatty acids and fatty acid moieties that are incorporated into lipid molecules within other lipid class(s) having any combination of features described herein such as lipid class, chain length, saturation/desaturation and/or position of any double-bond(s) as if the individual species embodying the various combinations of features were each expressly set forth herein.

In particular embodiments, the lipid profile comprises an evaluation of one or more lipid metabolites within one or more phospholipid classes. Further, this evaluation can include an assessment of the fatty acid moieties in the phospholipid class(es). For example, one or more lipid metabolites comprising a saturated, mono-unsaturated and/or polyunsaturated fatty acid moiety can be evaluated in one or more phospholipid classes. The lipid profile can additionally evaluate chain length within the phospholipid metabolites in one or more phospholipid classes (e.g., to assess short-, medium, long- and/or very long-chain polyunsaturated phospholipid(s)).

Further, in some embodiments, the lipid profile comprises an evaluation of one or more phospholipid metabolites within one or more phospholipid classes comprising an omega-3, omega-6 and/or omega-9 fatty acid moiety.

As another option, the ratio of two or more phospholipid metabolites within one or more phospholipid classes can be evaluated.

In particular embodiments of the invention, the lipid profile does not include a free fatty acid metabolite (but may include a lipid metabolite that comprises a fatty acid moiety). Alternatively, in some embodiments, the lipid profile can comprise one or more free fatty acids.

In other particular embodiments, the lipid profile does not include an arachidonic acid and/or other Δ5 desaturase products (e.g., adrenic acid [22:4n-6], tetracosatetraenoic acid [24:4n-6] and/or tetracosapentaenoic acid [24:5n-6]). In other representative embodiments, the lipid profile does include an arachidonic acid and/or other Δ5 desaturase products.

In other embodiments of the invention, the lipid profile does not include cholesterol. In other representative embodiments, the lipid profile does include cholesterol.

As a further option, the lipid profile can evaluate specific free fatty acids or fatty acid components within one or more lipid classes. Free fatty acids and fatty acid moieties that can be assessed in the lipid profile include but are not limited to: 14:0, 15:0, 16:0, 18:0, 20:0, 22:0, 24:0, 14:1n5, 16:1n7, 18:1n7, 18:1n9, 20:1n9, 20:3n9, 22:1n9, 24:1n9, 18:2n6, 18:3n6, 14:1n5, 20:1n15, 20:1n12, 18:3n3, 18:4n3, 20:3n3, 20:4n3, 20:5n3, 22:5n3, 22:6n3, 24:6n3, 18:2n6, 24:6n3, 18:2n6, 18:3n6, 20:2n6, 20:3n6, 20:4n6, 22:2n6, 22:4n6, 22:5n6, t16:1n7, t18:1n9, t18:2n6, dm16:0, dm18:0, dm18:1n9, dm18:1n7, total saturated fatty acids, total monounsaturated fatty acids, total polyunsaturated fatty acids, total LC fatty acids, total n3 (omega 3) fatty acids, total n6 fatty acids, total n7 fatty acids, total n9 fatty acids, and/or total dm fatty acids.

Further, in representative embodiments, the lipid profile can evaluate without limitation tetradecanoic acid, pentadecanoic acid, hexadecanoic acid, heptadecanoic acid, octadecanoic acid, eicosanoic acid, docosanoic acid, tetracosanoic acid, 9-tetradecenoic acid, 9-hexadecenoic acid, 11-octadecenoic acid, 9-octadecenoic acid, 11-eicosenoic acid, 5,8,11-eicosatrienoic acid, 13-docosenoic acid, 15-tetracosenoic acid, 9,12,15-octadecatrienoic acid, 6,9,12,15-octadecatetraenoic acid, 11,14,17-eicosatrienoic acid, 8,11,14,17-eicosictetraenoic acid, 5,8,11,14,17-eicosapentaenoic acid, 7,10,13,16,19-docosapentaenoic acid, 4,7,10,13,16,19-docosahexaenoic acid, 6,9,12,15,18,21-tetracoshexaenoic acid, 9,12-octadecadienoic acid, 6,9,12-octadecatrienoic acid, 11,14-eicosadienoic acid, 8,11,14-eicosatrienoic acid, 5,8,11,14-eicosicatetraenoic acid, 13,16-docsadienoic acid, 7,10,13,16-docosicatetraenoic acid, 4,7,10,13,16-docosapentaenoic acid, 9-trans-hexadecenoic acid, 9-trans-octadecenoic acid, 8-eicosaenoic acid, 5-eicosaenoic acid, and plasmalogen fatty acids, each as a free fatty acid or a fatty acid moiety incorporated into a larger lipid molecule.

In further representative embodiments, the lipid profile can evaluate without limitation cholesterol, lanosterol, lathosterol, cholestanol, dihydrocholesterol, 7-dehydrocholesterol, β-sitosterol, campesterol, desmosterol, stigmasterol, 7α-hydroxycholesterol, 4-cholesten-7α-ol-3-one, cholic acid, chenodeoxycholic acid, deoxycholic acid, lithocholic acid, ursodeoxycholic acid, glycocholic acid, taurocholic acid, glycodeoxycholic acid, taurodeoxycholic acid, glycodeoxycholic acid, taurodeoxycholic acid, glycolithocholic acid, taurolithocholic acid, glycoursodeoxycholic acid, 5b-cholestan-3b-ol, 5-cholesten-3b-ol, 5-cholestan-25a-methyl-3b-ol, 5-cholestan-24b-methyl-3b-ol, 5-cholesten-24b-ethyl-3b-ol, and/or 5,22-cholestadien-24b-ethyl-3b-ol.

In representative embodiments, the lipid profile can comprise any combination of the lipid metabolites set forth in the preceding paragraphs and, optionally, any of the metabolite ratios described herein.

Those skilled in the art will appreciate that the lipid profile can be relatively straight-forward (e.g., detecting the presence, amount and/or mole % within class) of relatively few (e.g., one, two, three or four) lipid metabolites or can be quite complex and encompass tens or even hundreds of lipid metabolites, optionally including a compositional analysis of the metabolites within one or more lipid classes. Thus, it will also be apparent that the lipid profiles and the methods described herein can be practiced to evaluate any combination of the lipid characteristics described herein.

In particular embodiments, the lipid profiles of the invention detect about 25% or more, about 40% or more, about 50% or more, about 60% or more, about 70% or more, about 75% or more, about 80% or more, about 85% or more, about 90% or more, about 95% or more, about 97% or more, about 98% or more, or about 99% or more of the lipid metabolites in a sample.

The lipid profile can be based on any suitable biological sample. The biological sample can be taken from a subject (e.g., a patient) and can be a centrally and/or peripherally derived biological sample, including without limitation body fluids, tissue, cellular, subcellular and/or extracellular biological samples. Illustrative tissues and cells include, but are not limited to, skeletal muscle tissue and cells, skin tissue and cells, neural tissue and cells including brain tissue and cells, spinal cord tissue and cells, eye tissue and cells (e.g., retinal cells), cardiac muscle tissue and cells, lung tissue and cells, pancreatic tissue and cells, liver tissue and cells, tissue and cells of the gastrointestinal system, adipose tissue and cells, and the like. Subcellular samples include one or more fractions and/or organelles of the foregoing cell types including but not limited to cytoplasm, nuclei, mitochondria, Golgi apparatus, endoplasmic reticulum, ribosomes, lysosomes, plasma membranes, endosomal fraction, and the like.

Samples, or biological samples, used to carry out the present invention are typically body fluids. Examples of body fluids include but are not limited to blood, plasma, serum, saliva, urine, lymph, semen, tears and cerebrospinal fluid.

The sample can be from any suitable subject. In particular embodiments the subject is a mammalian subject, which includes but is not limited to human, non-human primate, cattle, goats, sheep, horse, pig, dog, cat, rat, mouse, or hamster subjects and can further be male and/or female subjects. Human subjects include infants, children, adolescents, adult and/or elderly subjects. In some embodiments, the subject is an animal model for CVD. In other embodiments, the subject has or is at risk for CVD. The subject might be at risk for the disorder, for example, because of family history and/or environmental influences (including prior therapy).

The biological sample can be obtained at any time prior to commencing the statin treatment regimen (i.e., a baseline sample) or after the commencement of treatment (e.g., within about 2 hours, 4 hours, 6 hours, 12 hours, 1 day, 2 days, 3 days, 4 days, 5 days, 1 week, 2 weeks, 3 weeks, 4 weeks, 6 weeks, 8 weeks, 10 weeks, 12 weeks, 4 months, six months or longer of commencing the statin treatment regimen. In representative embodiments, the sample is taken any time from about 1, 2 or 3 days to about 1, 2, 3, 4, 5, 6, 7, 8 or 12 weeks after commencing the statin treatment regimen. In other embodiments, the sample is taken from about 1 week to about 2, 3, 4, 5, 6, 7, 8 or 12 weeks after commencing the statin treatment regimen, or from about 2 weeks to about 4, 5, 6, 7 or 8 weeks after commencing the statin treatment regimen, or from about 3 weeks to about 6, 8 or 12 weeks after commencing the statin treatment regimen, or from 4 weeks to 6, 8 or 12 weeks after starting the statin treatment regimen, or from about 6 weeks to about 8 or 12 weeks after commencing the statin treatment regimen. In other embodiments, the sample is taken at a timepoint more than about 2 hours, 4 hours, 6 hours, 12 hours, 1 day, 2 days, 3 days, 5 days, 1 week, 2 weeks, 6 weeks, 8 weeks, 10 weeks, 12 weeks, 4 months, six months or longer after commencing the statin treatment regimen.

Further, multiple samples (i.e., two or more) can be taken over time to monitor the responsiveness of the subject over the time period.

The lipid profile of the biological sample can be determined using any suitable method. The different classes of lipids and methods of detecting and optionally quantifying the same are well known in the art (e.g., thin layer chromatography, gas chromatography, liquid chromatography, mass and NMR spectrometry, and any combination thereof (e.g., GC/MS), and the like). One suitable method of detecting, and optionally quantifying, lipids in a biological sample employs stable isotope tracers to label the lipids. Methods of obtaining lipid profiles from biological samples have been described, see, e.g., U.S. Patent Publication Nos. 2007/0032969 (T. H. Barrett et al.); 2006/0088860 (S. M. Watkins and M. W. Wiest); 2005/0009005 (S. M. Watkins); 2004/0143461 A1 (S. M. Watkins) and Watkins et al. (2002) *J. Lipid Res.* 43(11): 1809-17.

One approach uses the methods and analytical tools developed by Lipomics Technologies (West Sacramento, Calif.). Lipomics Technologies has developed powerful tools to track sterol and bile acid metabolites as well as non-polar and polar lipids and map changes in disease to biochemical pathways. The Lipomics Profile provides comprehensive data on lipids present in a sample. A non-polar lipid analysis includes a complete quantification of the fatty acids from the free fatty acid, diglyceride, triglyceride, and cholesterol ester fractions of a sample. Additionally, Lipomics can determine the concentration of each fatty acid within an aggregate phospholipid fraction. A single non-polar TrueMass® analysis can produce as many as 200 individually quantified lipid metabolites. A polar lipid analysis can include a complete quantification of the fatty acids from the phospholipid classes including: lysophosphatidylcholine, sphingomyelin, phosphatidylcholine, phosphatidylserine, phosphatidylethanolamine and cardiolipin. A single polar lipid TrueMass® analysis can produce as many as 250 individually quantified lipid metabolites. Lipomics Technologies also has tools to track sterol and bile acid metabolites.

The lipidomics profile can be based on quantitative, semi-quantitative and/or qualitative analysis. For example, qualitative methods can be used to detect the presence or absence of a lipid metabolite(s) in a biological sample. Semi-quantitative methods can be used to determine a level of a particular lipid metabolite(s) above a threshold value or to determine ratios of different lipid metabolites, without assigning an absolute or relative numerical value. Quantitative methods can be used to determine a relative or absolute amount of a particular lipid metabolite(s) in the biological sample.

In semi-quantitative methods, a threshold or cutoff value can be determined by any means known in the art, and is optionally a predetermined standard. In particular embodiments, the threshold value is predetermined in the sense that it is fixed, for example, based on previous experience with the assay and/or a population of subjects that are responsive and/or non-responsive to statin treatment. Alternatively, the term "predetermined standard" can also indicate that the method of arriving at the threshold is predetermined or fixed even if the particular value varies among assays or may even be determined for every assay run.

The lipidomics analysis of the invention can generate high-density data sets that can be evaluated using informatics approaches. High data density informatics analytical methods are known and software is available to those in the art, e.g., cluster analysis (Pirouette, Informetrix), class prediction (SIMCA-P, Umetrics), principal components analysis of a computationally modeled dataset (SIMCA-P, Umetrics), 2D cluster analysis (GeneLinker Platinum, Improved Outcomes Software), and metabolic pathway analysis (biotech.icmb.utexas.edu). The choice of software packages offers specific tools for questions of interest (Kennedy et al., Solving Data Mining Problems Through Pattern Recognition. Indianapolis: Prentice Hall PTR, 1997; Golub et al., (2999) *Science* 286:531-7; Eriksson et al., Multi and Megavariate Analysis: Principles and Applications: Umetrics, Umea, 2001).

In general, any suitable mathematic analyses can be used to evaluate one, two, three, four, five, six, seven, eight, nine, ten or more lipid metabolites in a lipid profile with respect to a CVD. For example, methods such as multivariate analysis of variance, multivariate regression, and/or multiple regression can be used to determine relationships between dependent variables (e.g., clinical measures) and independent variables (e.g., levels of lipid metabolites). Clustering, including both hierarchical and nonhierarchical methods, as well as nonmetric Dimensional Scaling can be used to determine associations among variables and among changes in those variables.

In addition, principal component analysis is a common way of reducing the dimension of studies, and can be used to interpret the variance-covariance structure of a data set. Principal components may be used in such applications as multiple regression and cluster analysis. Factor analysis is used to describe the covariance by constructing "hidden" variables from the observed variables. Factor analysis may be considered an extension of principal component analysis, where principal component analysis is used as parameter estimation along with the maximum likelihood method. Furthermore, simple hypothesis such as equality of two vectors of means can be tested using Hotelling's T squared statistic.

Pharmacological Methods.

The present invention can be practiced in the field of predictive medicine for the purposes of predicting or monitoring response to therapy (particularly statin therapy), monitoring the development of side effects and/or predicting efficacy and/or side effects of a particular treatment (such as a statin treatment regimen), and the like.

Samples, subjects (including subjects with CVD and subjects at risk for CVD) and lipid profiles are as discussed herein. The diagnostic methods of the invention can be practiced with any combination of features disclosed herein. For example, the lipid profile can evaluate any combination of lipid metabolites including lipid class, fatty acid chain length, fatty acid saturation/desaturation, and/or position of any double-bonds.

For methods of predicting whether a subject is a good candidate for a statin therapy (e.g., will show a positive response), the sample can be obtained at any time prior to commencing the statin treatment regimen (i.e., a baseline sample). For methods of determining whether a subject is responding to treatment, the sample can be obtained at any suitable point after the commencement of treatment (e.g., within about 2 hours, 4 hours, 6 hours, 12 hours, 1 day, 2 days, 3 days, 4 days, 5 days, 1 week, 2 weeks, 3 weeks, 4 weeks, 6 weeks, 8 weeks, 10 weeks, 12 weeks, 4 months, six months or longer of commencing the statin treatment regimen. In representative embodiments, the sample is taken any time from about 1, 2 or 3 days to about 1, 2, 3, 4, 5, 6, 7, 8 or 12 weeks after commencing the statin treatment regimen. In other embodiments, the sample is taken from about 1 week to about 2, 3, 4, 5, 6, 7, 8 or 12 weeks after commencing the statin treatment regimen, or from about 2 weeks to about 4, 5, 6, 7 or 8 weeks after commencing the statin treatment regimen, or from about 3 weeks to about 6, 8 or 12 weeks after commencing the statin treatment regimen, or from about 4 weeks to about 6, 8 or 12 weeks after commencing the statin treatment regimen, or from about 6 weeks to about 8 or 12 weeks after commencing the statin treatment regimen. In other embodiments, the sample is taken at a timepoint more than about 2 hours, 4 hours, 6 hours, 12 hours, 1 day, 2 days, 3 days, 5 days, 1 week, 2 weeks, 6 weeks, 8 weeks, 10 weeks, 12 weeks, 4 months, six months or longer after commencing the statin treatment regimen.

In particular embodiments, the lipid profile evaluates lipid metabolites in two or more lipid classes (e.g., in three or more, four or more, five or more, six or more, seven or more, eight or more classes, etc).

In some methods of the invention, the lipid profile evaluates two or more lipids within one or more lipid classes. Thus, the invention can be practiced to evaluate multiple lipid metabolites, which can be present in the same class, and optionally belong to different subclasses (e.g., different fatty acid moieties), or can belong to two or more lipid classes (e.g., three or more, four or more, five or more, six or more, seven or more, eight or more lipid classes etc).

As discussed herein, the methods can be partially or completely quantitative and measure the amount (e.g., a quantitative amount such as weight or moles) of one or more (e.g., optionally all) of the lipid metabolites in the profile. In other embodiments, the methods can be partially or completely relative and, for example, comprise determining the weight % or mole % within class of one or more (optionally all) of the lipid metabolites in the profile.

According to some aspects of the invention, ratios between two or more lipid metabolites (within the same and/or different classes) are determined.

As also discussed herein, the lipid profile can be based on measurements of individual metabolites, ratios between two or more metabolites, or a combination of both.

As noted above, an aspect of the invention is a method of correlating a lipid profile with a positive or negative response to a statin treatment regimen, the method comprising: obtaining a lipid profile of a sample from a mammalian subject following commencement of the treatment regimen; and correlating the lipid profile in the sample with a positive or negative response to the treatment regimen. In some embodiments the subject is afflicted with or at risk for a CVD, and the treatment regimen is for treating or preventing the CVD. In some embodiments of the foregoing, the lipid profile comprises at least one or at least two lipids or lipid metabolites, wherein the lipid metabolite(s) comprise one or more or two or more of the following: triglycerides, free fatty acids, diacylglyercols, fatty-acid derived phospholipids, sphingolipids, glycolipids, terpenoids, cholesterol, cholesterol esters, steroids, bile acids, primary bile acids, secondary bile acids, oxysterols, sterols, endogenous sterols, phytosterols, oxysterols, and eicosanoids.

In some embodiments of the foregoing, the lipid profile includes at least one lipid metabolite; a decrease in at least one or at least two lipid metabolites in a sample from the subject as compared to a sample from the subject prior to commencement of the statin treatment regimen indicating a positive response by the subject to the treatment regimen, and/or an increase or no change in at least one or at least two lipid metabolites in a sample from the subject as compared to a sample from the subject prior to commencement of the statin treatment regimen indicating a negative response by the subject to the treatment regimen, wherein the at least one or at least two lipid metabolites comprise CELC, FCLC, PCLC, PELC, DGn6, DG18.1n9, CE18.2n6, DG18.2n6, PE18.0, PE18.2n6, PE20.3n6, DG20.3n9, PC20.3n9, PC20.4n3, FA22.2n6, TGLC, PC18:2n6, PC18:3n3, PC20:3n6, LY18:0, and/or LY20:4n3.

In representative embodiments of the foregoing, the lipid profile includes at least one or at least two lipid metabolites; an increase in the at least one or at least two lipid metabolites in a sample from the subject as compared to a sample from the subject prior to commencement of the treatment regimen indicating a positive response by the subject to the statin treatment regimen and/or a decrease or no change in the at least one or at least two lipid metabolites in a sample from the subject as compared to a sample from the subject prior to commencement of the treatment regimen indicating a negative response by the subject to the statin treatment regimen, wherein the at least one or at least two lipid metabolites comprise CE24.0, CE22.1n9, TG18.4n3, LY18.3n6, CE18.1n7, CE18.0, CE22.6n3, PC18.1n7, CE20.4n6, DG18.0, DGSFA, DGLC, PC20:4n6, PC22:1n9, PC22:6n3, and/or TG18:3n6.

In embodiments of the invention, the lipid profile includes at least one or at least two lipid metabolites; an increase in said at least one or at least two lipid metabolites in a sample from said subject as compared to a sample from said subject prior to commencement of said statin treatment regimen indicating a positive response by said subject to said treatment regimen and/or a decrease in said at least one or at least two lipid metabolites in a sample from said subject as compared to a sample from said subject prior to commencement of said statin treatment regimen indicating a negative response by said subject to said treatment regimen, wherein the at least one or at least two lipid metabolites comprise: 4-cholesten-7a-ol-3-one, and/or 7α-hydroxycholesterol.

In still other representative embodiments of the foregoing, the lipid profile includes at least one or at least two lipid metabolites; a decrease in at least one or at least two lipid metabolites in a sample from the subject as compared to a sample from the subject prior to commencement of the statin treatment regimen indicating a positive response by the subject to the treatment regimen, and/or an increase or no change in at least one or at least two lipid metabolites in a sample from the subject as compared to a sample from the subject prior to commencement of the statin treatment regimen indicating a negative response by the subject to the treatment regimen, wherein the at least one or at least two lipid metabolites comprise cholesterol, lanosterol, 7-dehydrocholesterol, desmosterol, and coprostanol.

In embodiments of the invention, the lipid profile includes at least one or at least two lipid metabolites; a decrease in said at least one or at least two lipid metabolites in a sample from said subject as compared to a sample from said subject prior to commencement of said statin treatment regimen indicating a positive response by said subject to said treatment regimen and/or and increase or no change in said at least one or at least two lipid metabolites in a sample from said subject as compared to a sample from said subject prior to commencement of said statin treatment regimen indicating a negative response by said subject to said treatment regimen; wherein said at least one or at least two lipid metabolites comprise: β-sitosterol, campesterol, stigmasterol, coprostanol, 7-dehydrocholesterol, cholestanol, desmosterol, lanosterol, and/or lathosterol.

In particular embodiments, the method can utilize any combination of the response markers in the preceding paragraphs and, optionally, the metabolite ratios disclosed herein.

In some embodiments of the foregoing, the method further comprises, when a positive response is correlated to the lipid profile, continuing the treatment regimen in the subject.

In some embodiments of the foregoing, the method further comprises, when a negative response to the treatment regimen is correlated to the lipid profile, discontinuing the treatment regimen and, optionally, then commencing a different statin treatment regimen in the subject. The different statin treatment regimen can comprise: altering the dose of the statin treatment regimen, administering a different statin to the subject, administering an additional active agent to the subject in combination with the statin, or a combination thereof.

A further aspect of the invention is a method of correlating a lipid profile with a positive or negative response to a statin treatment regimen, the method comprising: obtaining a lipid profile of a sample from a mammalian subject before commencement of the treatment regimen; and correlating the lipid profile in the sample with a positive or negative response to the treatment regimen. In some embodiments, the subject is afflicted with or at risk for CVD, and the treatment regimen is to treat or prevent the CVD. In some embodiments, the lipid profile comprises at least one or at least two lipids or lipid metabolites, wherein the lipid(s) or lipid metabolite(s) belong to one or more of the following: triglycerides, flee fatty acids, diacylglyercols, fatty-acid derived phospholipids, sphingolipids, glycolipids, terpenoids, cholesterol, cholesterol esters, steroids, bile acids, primary bile acids, secondary bile acids, oxysterols, sterols, endogenous sterols, phytosterols, and eicosanoids.

In some embodiments of the foregoing: the lipid profile includes at least one or at least two lipid metabolites; an increased level of the at least one or at least two metabolites in a sample from the subject as compared to a predetermined standard indicating a positive response to the statin treatment regimen; a decreased level of the at least one or at least two metabolites in a sample from the subject as compared to a predetermined standard indicating a negative response to the statin treatment regimen; wherein the at least one or at least two metabolites comprise: DG18:1n9 and/or LY22:1n9.

The predetermined standard can be determined by any suitable method known in the art. For example, the predetermined standard can be based on the level of the metabolite in any suitable control subject or population of subjects as would be known to those skilled in the art. For example, the predetermined standard can be based on the average level of the metabolite in samples from a control set of subjects. In particular embodiments, the standard is predetermined in the sense that it is fixed, for example, based on previous experience with the assay and/or a population of subjects that are responsive and/or nonresponsive to statin treatment. Alternatively, the term "predetermined standard" can also indicate that the method of arriving at the value is predetermined or fixed even if the particular value varies among assays or may even be determined for every assay run.

In some embodiments of the foregoing, the lipid profile includes at least one or at least two lipid metabolites; a decreased level of the at least one or at least two metabolites in a sample from the subject as compared to a predetermined standard indicating a positive response to the statin treatment regimen; an increased level of the at least one or at least two metabolites in a sample from the subject as compared to a predetermined standard indicating a negative response to the statin treatment regimen, wherein the at least one or at least two metabolites comprise: CE16:0, CE20:3n9, CE22:5n6, DG14:0, DG16:0, DG14:1n5, LY18:3n6, PE24:1n9, PC20:0, PC22:0, PC18:1n9, TG22:1n9, and/or TG18:4n3.

A still further aspect of the invention is a method of correlating a lipid profile with a positive or negative response to a statin treatment regimen, the method comprising: obtaining a lipid profile of a sample from a mammalian subject before commencement of the treatment regimen; and correlating the lipid profile in the sample with a positive or negative response to the treatment regimen. In some embodiments, the subject is afflicted with or at risk for a CVD, and the treatment regimen is to treat or prevent the CVD. In some embodiments, the lipid profile comprises at least one or at least two lipid metabolites comprising: cholesterol, lanosterol, lathosterol, cholestanol, 7-dehydrocholesterol, β-sitosterol, campesterol, desmosterol, stigmasterol, 7α-hydroxycholesterol, 4-cholesten-7α-ol-3-one, cholic acid, chenodeoxycholic acid, deoxycholic acid, lithocholic acid, ursodeoxycholic acid, glycocholic acid, taurocholic acid, glycodeoxycholic acid, taurodeoxycholic acid, glycodeoxycholic acid, taurodeoxycholic acid, glycolithocholic acid, taurolithocholic acid, and/or glycoursodeoxycholic acid.

In some embodiments of the foregoing the lipid profile includes at least one or at least two lipid metabolites; an increased level of the at least one or at least two metabolites in a sample from the subject as compared to a predetermined standard indicating a positive response to the statin treatment regimen; a decreased level of the at least one or at least two metabolites in a sample from the subject as compared to a predetermined standard indicating a negative response to the statin treatment regimen; wherein the at least one or at least two metabolites comprise: lithocholic acid, taurolithocholic acid, taurodeoxycholic acid, coprostanol, glycolithocholic acid, glycodeoxycholic acid, and/or deoxycholic acid.

In embodiments of the foregoing the lipid profile includes at least one or at least two lipid metabolites; an increased level of said at least one or at least two metabolites in a sample from said subject as compared to a predetermined standard indicating a positive response to said statin treatment regimen; a decreased level of said at least one or at least two metabolites in a sample from said subject as compared to a predetermined standard indicating a negative response to said statin treatment regimen; wherein said at least one or at least two metabolites comprise: 4-cholesten-7a-ol-3-one, 7α-hydroxycholesterol, 7-dehydrocholesterol, cholestanol, desmosterol, lanosterol, and/or lathosterol.

In some embodiments of the foregoing, the lipid profile includes at least one or at least two lipid metabolites; a decreased level of the at least one or at least two metabolites in a sample from the subject as compared to a predetermined standard indicating a positive response to the statin treatment regimen; an increased level of the at least one or at least two metabolites in a sample from the subject as compared to a predetermined standard indicating a negative response to the statin treatment regimen, wherein the at least one or at least two metabolites comprise: cholic acid and/or chenodeoxycholic acid.

In embodiments of the foregoing, said lipid profile includes at least one or at least two lipid metabolites; a decreased level of said at least one or at least two metabolites in a sample from said subject as compared to a predetermined standard indicating a positive response to said statin treatment regimen; an increased level of said at least one or at least two metabolites in a sample from said subject as compared to a predetermined standard indicating a negative response to said statin treatment regimen, wherein said at least one or at least two metabolites comprise: β-sitosterol, campesterol, stigmasterol, and coprostanol.

In some embodiments of the invention, the method further comprises, when a positive response is correlated to the lipid profile, commencing the treatment regimen in the subject.

In some embodiments of the foregoing, the method further comprises, when a negative response to the treatment regimen is correlated to the lipid profile, evaluating a different statin treatment regimen. The different statin treatment regimen can comprise: altering the dose of the statin treatment regimen, administering a different statin to the subject, administering an additional active agent to the subject in combination with the statin, or a combination thereof.

In particular embodiments, the method can utilize any combination of the predictive markers in the preceding paragraphs and, optionally, the metabolite ratios disclosed herein.

Metabolite ratios that reflect rates of cholesterol synthesis, degradation and/or absorption can also be used as predictive and/or response markers alone or in combination with measures of individual metabolite(s) as described herein. In particular embodiments, the subject is afflicted with or at risk for CVD, and the treatment regiment is for treating or preventing CVD.

In embodiments of the invention, metabolite ratios indicating a relatively high level of cholesterol synthesis pre-treatment as compared with a predetermined standard indicate that the subject will have a positive response to statin treatment and metabolite ratios indicating a decrease in cholesterol synthesis post-treatment indicate that the subject is having a positive response to treatment.

Nonlimiting examples of ratios include:
Synthetic pathway 1: Ratio of desmosterol/lanosterol
Synthetic pathway 2: Ratio of lathosterol/lanosterol
Synthetic pathway 2 (version 2): lathosterol+7-dehydrocholesterol/lanosterol
Other ratios based on cholesterol synthetic pathways that correlate with response to statin (at baseline and/or after treatment commences) include:
Ratio of 7-dehydrocholesterol/cholesterol
Ratio of cholestanol/cholesterol
Ratio of desmosterol/cholesterol
Ratio of lanosterol/cholesterol
Ratio of lathosterol/cholesterol In embodiments of the invention, a relatively high value for one or more of these ratios in pre-treatment samples as compared with a predetermined standard indicates that the subject will have a positive response to statin treatment; and a relatively low value for one or more of these ratios in pre-treatment samples as compared with a predetermined standard indicates that the subject will have a negative response to statin treatment. In other representative embodiments, an increase or no change in one or more of these metabolite ratios in post-treatment samples indicates that the subject is having a negative response to treatment; and a decrease in one or more of these metabolite ratios in post-treatment samples indicates that the subject is having a positive response to treatment.

Accordingly, in embodiments of the invention, a metabolite ratio determined from a sample from a subject prior to treatment that reflects a relatively high level of cholesterol synthesis as compared with a predetermined standard (as defined herein) indicates that the subject will have a positive response to statin treatment, and/or a metabolite ratio that reflects a relatively low level of cholesterol synthesis prior to treatment as compared with a predetermined standard indicates that the subject will have a negative response to statin treatment.

In embodiments of the invention, a metabolite ratio determined from a sample from a subject following commencement of a statin treatment regimen that reflects a decrease in cholesterol synthesis as compared with the metabolite ratio determined from a sample from the subject prior to commencement of the statin treatment regimen indicates a positive response by the subject to the treatment regimen and/or a metabolite ratio determined from a sample from a subject following commencement of a statin treatment regimen that reflects an increase or no change in cholesterol synthesis as compared with the metabolite ratio determined from a sample from the subject prior to commencement of the statin treatment regimen indicates a negative response by the subject to the treatment regimen.

Cholesterol absorption is negatively correlated with statin response and can be evaluated by looking at metabolite ratios at baseline and/or after treatment commences. Nonlimiting examples of such ratios include.
Ratio of β-sitosterol/cholesterol
Ratio of campesterol/cholesterol
Ratio of fucosterol/cholesterol
Ratio of stigmasterol/cholesterol
Ratio of coprostanol/cholesterol In embodiments of the invention, a relatively high value of one or more of these ratios pre-treatment as compared with a predetermined standard indicates that the subject will have a positive response to statin treatment, and a relatively low value of one or more of these ratios pre-treatment as compared with a predetermined standard indicates that the subject will have a negative response to statin treatment. In representative embodiments, an increase in one or more of these ratios post-treatment indicates that the subject is having a positive response to statin treatment, and a decrease in one or more of these ratios post-treatment indicates that the subject is having a negative response to statin treatment. In embodiments of the invention, metabolite ratios indicating that a subject has a relatively high level of cholesterol absorption pre-treatment as compared with a predetermined standard indicate that the subject will have a positive response to statin treatment. In other embodiments, metabolite ratios indicating that the subject has an increase in cholesterol absorption post-treatment indicates that the subject is having a positive response to treatment.

Accordingly, in embodiments of the invention, a metabolite ratio determined from a sample from a subject prior to treatment that reflects a relatively high level of cholesterol absorption as compared with a predetermined standard (as defined herein) indicates that the subject will have a positive response to statin treatment, and a metabolite ratio that reflects a relatively low level of cholesterol absorption prior to treatment as compared with a predetermined standard indicates that the subject will have a negative response to statin treatment.

Further, a metabolite ratio determined from a sample from a subject following commencement of a statin treatment regimen that reflects a decrease or no change in cholesterol absorption as compared with the metabolite ratio determined from a sample from the subject prior to commencement of the statin treatment regimen indicates a negative response by the subject to the treatment regimen and/or a metabolite ratio determined from a sample from a subject following commencement of a statin treatment regimen that reflects an increase in cholesterol absorption as compared with the metabolite ratio determined from a sample from the subject prior to commencement of the statin treatment regimen indicates a positive response by the subject to the treatment regimen.

Cholesterol degradation pathways can also be used to evaluate responsiveness (at baseline and/or after treatment commences) to statins. In particular embodiments, metabolite ratios relevant to cholesterol degradation as compared with a predetermined standard that reflect relatively low levels of cholesterol degradation at baseline indicate that the subject will have a positive response to statin treatment. In other embodiments, metabolite ratios indicating an increase in cholesterol degradation post-treatment indicate a positive response to statin treatment. Nonlimiting examples of metabolite ratios relevant to cholesterol degradation include:
Ratio of any bile acid such as cholic acid/cholesterol
Ratio of primary bile acids/cholesterol
Ratio of secondary bile acids/cholesterol In embodiments of the invention, a relatively high value for one or more of these ratios as compared with a predetermined standard in a subject pre-treatment indicates that the subject will have a negative response to statin treatment, and a relatively low value for one or more of these ratios as compared with a predetermined standard in a subject pre-treatment indicates that the subject will have a positive response to statin treatment. In embodiments of the invention, an increase in one or more of these ratios post-treatment indicates that the subject is having a positive response to statin treatment, and a decrease or no change in one or more of these ratios post-treatment indicates that the subject is having a negative response to statin treatment.

Accordingly, in embodiments of the invention, a metabolite ratio determined from a sample from a subject prior to treatment that reflects a relatively high level of cholesterol degradation as compared with a predetermined standard (as defined herein) indicates that the subject will have a negative response to statin treatment, and/or a metabolite ratio that reflects a relatively low level of cholesterol degradation prior to treatment as compared with a predetermined standard indicates that the subject will have a positive response to statin treatment.

Further, in other embodiments, a metabolite ratio determined from a sample from a subject following commencement of a statin treatment regimen that reflects an increase in cholesterol degradation as compared with the metabolite ratio determined from a sample from the subject prior to commencement of the statin treatment regimen indicates a positive response by the subject to the treatment regimen and/or a metabolite ratio determined from a sample from a subject following commencement of a statin treatment regimen that reflects a decrease or no change in cholesterol degradation as compared with the metabolite ratio determined from a sample from the subject prior to commencement of the statin treatment regimen indicates a negative response by the subject to the treatment regimen.

In addition, the ratio of secondary bile acids/primary bile acids can be used to predict or to evaluate response (e.g., at baseline and/or after treatment commences) to statins. Relatively low ratios of secondary bile acid(s)/primary bile acid(s) prior to treatment indicate a positive response to statin treatment, and a relatively high ratio of secondary bile acid(s)/primary bile acid(s) prior to treatment indicate a negative response to statin treatment. Further, a relatively high ratio of secondary bile acid(s)/primary bile acid(s) post-treatment indicate a positive response to statin treatment, and a relatively low ratio of secondary bile acid(s)/primary bile acid(s) post-treatment indicate a negative response to statin treatment. Illustrations of such ratios include:

Ratio of secondary bile acids/primary bile acids; and/or
Ratio of one or more secondary bile acids/one or more primary bile acids In embodiments of the invention, a decrease in a secondary bile acid(s)/primary bile acid(s) ratio determined from a sample from a subject prior to treatment as compared with a predetermined standard (as defined herein) indicates that the subject will have a positive response to statin treatment, and/or an increase in secondary bile acid(s)/primary bile acid(s) ratio prior to treatment as compared with a predetermined standard indicates that the subject will have a negative response to statin treatment.

Further, in embodiments of the invention an increase in the secondary bile acid(s)/primary bile acid(s) ratio determined from a sample from a subject following commencement of a statin treatment regimen as compared with the ratio determined from a sample from the subject prior to commencement of the statin treatment regimen indicates a positive response by the subject to the treatment regimen and/or a decrease or no change in the secondary bile acid(s)/primary bile acid(s) ratio determined from a sample from a subject following commencement of a statin treatment regimen indicates a negative response by the subject to the treatment regimen.

In some embodiments of the invention, the method further comprises, when a positive response is correlated to the lipid profile, commencing the treatment regimen in the subject.

In some embodiments of the foregoing, the method further comprises, when a negative response to the treatment regimen is correlated to the lipid profile, evaluating a different statin treatment regimen. The different statin treatment regimen can comprise: altering the dose of the statin treatment regimen, administering a different statin to the subject, administering an additional active agent to the subject in combination with the statin, or a combination thereof.

In particular embodiments, the method can utilize any combination of the metabolite ratios in the preceding paragraphs.

Any suitable assay format can be used to carry out the invention. Hence, the methods and uses herein may comprise detecting one or more ratios between lipid metabolites in a pathway. In some embodiments the lipid profile can evaluate lipid metabolites in two or more lipid classes; and/or two or more lipid metabolites within one or more lipid classes. In some embodiments, an amount of a lipid metabolite can be detected. Some embodiments may comprise detecting a mole % within class of a lipid metabolite, etc.

Databases, User Interfaces, Computer-Readable Media, and Computer Systems.

The invention further provides a computer-readable medium having contained thereon a lipidomic database, wherein the database contains a plurality of records, each record including data (e.g., quantitative or relational) for one or a plurality of metabolites from a biological sample. In particular embodiments, the database is obtained from subjects having CVD or at risk for developing CVD. Further, the database may reflect samples taken prior to and/or after commencement of a treatment regimen. Further, the database can optionally indicate the severity of the subject's condition, the efficacy or lack of efficacy of a treatment regimen, and/or side effects associated with a treatment regimen.

Such databases may be on a computer-readable storage medium, and may be formatted for processing by a computer. Data included in the databases may include any or all of the following:

information that provides for unique identification of data from a sample;
raw measurements of individual lipid metabolites;
transformed measurements of individual metabolites (which have been subject to one or more mathematical transformations from raw data);
basic information about the biological sample (e.g., species, tissue, preparation date, etc.);
genetic information about the subject from which the biological sample was taken (e.g., genotype of a knockout or otherwise engineered animal);
information about any previous diagnosis with a CVD;
health or care history of the subject from which the sample was taken (e.g., long term care strategies, chronic conditions, etc.);
information about the treatment of the subject from which the biological sample was taken (e.g., drug application, feeding schedule or diet, stressors, environment, or toxins);
information about the harvesting of the individual sample and/or the processing of the sample;
information about the individual lipid metabolites (e.g., biochemical or biological characteristics);
information about one or more of the implicated metabolic pathways;
one or more metabolite fingerprints that are associated with a CVD, treatment, genotype, and/or drug application (e.g., to serve as a baseline or control sample);
information linking the treated or test samples to their experimental control samples;
information about the analytical process of producing data; and/or
information about the laboratory, investigator and analytical chemists responsible for producing the data.

The provided databases may serve to organize lipid metabolite information, or any of the other information types indicated, in one or more tables. Such tables are readily translatable into database languages such as SQL, and the databases optionally can be integrated with an on-line Internet site containing results of user-defined metabolite analyses.

Another embodiment is a user interface for operatively working with a processor to affect operation of a database as provided herein, where the user interface includes means for providing settings for selecting a set of samples, means for providing settings for selecting a set of conditions, means for providing settings for selecting a set of lipid metabolites, and means for displaying lipidomic profiles corresponding to the selected samples and conditions, wherein each displayed lipidomic profile includes the measurement (e.g., quantitative or relational) of the selected lipid metabolite(s). Optionally, the user interface can further include a display area that displays the measurement of a lipid metabolite within the lipidomic profiles of the selected samples and conditions. Optionally, the user interface can further include means for comparing lipidomic profiles corresponding to a first set of selected samples and conditions to the lipidomic profiles corresponding to a second set of selected samples and conditions, and means for displaying the comparison.

Another embodiment of the invention provides a computer implemented method for operating a relational database which method involves creating a profile table including a lipidomic profile from a biological sample from an individual having a condition, wherein the lipidomic profile comprises a quantified measurement of a lipid metabolite and wherein the quantified measurement is obtained using an internal standard for the lipid metabolite so that the quantified measurement is integratable into a database, creating a sample item table including a sample record for the quantified lipidomic profile, creating a condition item table including a condition record for the quantified lipidomic profile, and storing data in the profile table, the sample item table, and the condition item table, wherein each quantified lipidomic profile corresponds to a sample record and a condition record.

Yet a further embodiment is a computer system for analyzing quantitative lipidomic information, which system includes a processor; and a storage medium storing a relational database accessible by the processor, wherein the storage medium has stored thereon: the relational database comprising: a first table including a plurality of records, wherein at least one of the records includes quantitative data for a plurality of lipid metabolites. Specific examples of such computer systems include a processor, and a storage medium storing a relational database accessible by the processor, wherein the storage medium having stored thereon a relational database comprising a profile table including a quantified lipidomic profile from a biological sample of a condition, wherein the quantified lipidomic profile comprises a quantified measurement of a lipid metabolite and wherein the quantified measurement is obtained using an internal standard for the metabolite so that the quantified measurement is integratable into the relational database, a sample item table including a sample record for the quantified lipidomic profile, and a condition item table including a condition record for the quantified lipidomic profile.

Methods of analyzing/mining the databases of the invention and presentation of the data provided therein (i.e., format of data output) are known in the art, see, e.g., U.S. Patent Publication Nos 2007/0032969 (T. H. Barrett et al.); 2006/0088860 (S. M. Watkins and M. W. Wiest); 2005/0009005 (S. M. Watkins); 2004/0143461 A1 (S. M. Watkins).

Having described the present invention, the same will be explained in greater detail in the following examples, which are included herein for illustration purposes only, and which are not intended to be limiting to the invention.

Example 1

Changes in Lipid Profile Following Simvastatin Treatment

We evaluated lipid profiles of 48 subjects selected from the Pharmacogenetics and Risk of Cardiovascular Disease (PARC) study. Subjects were selected from the larger study population of 944 participants (335 African-Americans and 609 whites), with a baseline total serum cholesterol level of 160 to 400 mg/dl. Participants were followed for a total of 6 weeks on simvastatin therapy (40 mg at bedtime). Twenty-four subjects drawn from the top 10% of responders and 24 age-, gender-, and race-matched subjects from the bottom 10% of responders. Response was defined as percent change in LDL cholesterol from baseline to end of treatment. Samples used in this study were collected at baseline and at 6 weeks of therapy.

Experimental

Data Reporting. Lipids measured included, butyrobetaine, L-carnitine, cholesterol, cholesterol esters (CE), diglycerides (DG), free cholesterol (FC), free fatty acids (FA), lysophosphatidylcholine (LY), phosphatidylcholine (PC), phosphatidylethanolamine (PE) and triglycerides (TG). For CE, DG, FA, LY, PC, PE and TG lipid classes the following fatty acid components were quantified as a proportion of total fatty acids within the lipid class: 14:0, 15:0, 16:0, 18:0, 20:0, 22:0, 24:0, 14:1n5, 16:1n7, 18:1n7, 18:1n9, 20:1n9, 20:3n9, 22:1n9, 24:1n9, 18:2n6, 18:3n6, 20:2n6, 20:3n6, 20:4n6, 22:2n6, 22:4n6, 22:5n6, 18:3n3, 18:4n3, 20:3n3, 20:4n3, 20:5n3, 22:5n3, 22:6n3, 24:6n3, plasmalogen derivatives of 16:0, 18:0, 18:1n7 and 18:1n9, t16:1n7 t18:1n9 t18:2n6. The term "LC" indicates the value shown is the total concentration of the lipid class expressed as nMoles per gram of serum or plasma. Thus, the abbreviation PC18:2n6 indicates the percentage of plasma or serum phosphatidylcholine comprised of linoleic acid (18:2n6), and the term TGLC indicates the absolute amount of triglyceride present in plasma or serum.

Statistical Methods. Before undertaking analysis, the data was cleaned by outlier removal and removal of uninformative metabolites. Outliers were identifies as those observation more than three standard deviations from the mean. Metabolites were determined to be uninformative if over ⅔rds of the observations were below the limit of detection and the pattern of observations falling below this limit was not related to the outcome.

Results of t-tests were used in order to reduce the number of metabolites being modeled. Metabolites that significantly changed at a p-value of 0.05 in either high or low responders were examined using ANOVA and ANCOVA.

A simple one-way ANOVA was used to evaluate the difference in lipid changes between high and low responders. From this analysis, contrasts were calculated for the comparison of low to high responders. In addition, an ANCOVA model was used to evaluate the difference in response adjusting for baseline concentrations of the metabolite and the time the samples were run. The outcome was change from baseline to post-treatment, baseline concentration was the covariate, response (high=1, low=0) and group (first=0, second=1) were included as factors, and an interaction term between baseline and response was included.

The column labeled "estimate" is the difference between the change from pre to post in high and low responders (high minus low). The standard error, t-statistic, p-value, and 95% confidence bounds of this estimate are also included (Lower.CI and Upper.CI).

Results

Changes in Lipid Class Concentrations. The concentrations of total cholesterol esters, phosphatidylethanolamine, phosphatidylcholine, and free cholesterol were significantly different between responders and non-responders following treatment with simvastatin. Contrasts between the average changes in high versus low responders were calculated with 95% confidence intervals. High responders showed a much larger decrease in these four lipid classes. The difference between the two groups was −1141 (−1470.9, −811.9) for total cholesterol ester, −27.56 (−51.6, −3.5) in total phosphatidylethanolamine, −345.7 (−602.7, −88.7) in total phosphatidylcholine and −502.3 (−699.0, 305.7) in free cholesterol. Triglycerides dropped in both high and low responders, with no significant difference in magnitude.

TABLE 1

Estimate and inference of the difference between change in high and low responders in lipid classes.

| Metabolites | Estimate | ANOVA | | | | |
|---|---|---|---|---|---|---|
| | | Std. Err | T. value | P. value | Lower. CI | Upper. CI |
| CELC | −1137.557 | 163.8033 | −6.9447 | 0 | −1467.4738 | −807.6403 |
| DGLC | 2.4502 | 3.4484 | 0.7105 | 0.481 | −4.4952 | 9.3955 |
| TGLC | −128.3429 | 138.3086 | −0.9279 | 0.3584 | −406.9108 | 150.225 |
| PELC | −27.3997 | 11.8624 | −2.3098 | 0.0255 | −51.2918 | −3.5077 |
| FCLC | −502.3359 | 97.1314 | −5.1717 | 0 | −697.8514 | −306.8205 |
| PCLC | −347.3967 | 125.6758 | −2.7642 | 0.0091 | −602.8007 | −91.9926 |

Changes in the Fatty Acid Composition of Lipid Classes. Compositional changes in cholesterol esters included increases in 18:0, 24:0, 18:1n7, 22:1n9, 20:4n6 and 22:6n3 in the high responders over the low responders. CE18:2n6 decreased significantly more in high than low responders.

TABLE 2

Estimate and inference of the difference between change in high and low responders in cholesterol ester.

| Metabolites | Estimate | ANOVA | | | | |
|---|---|---|---|---|---|---|
| | | Std. Err | T. value | P. value | Lower. CI | Upper. CI |
| CE18.0 | 0.1411 | 0.0498 | 2.8322 | 0.0069 | 0.0408 | 0.2415 |
| CE24.0 | 0.0212 | 0.0068 | 3.1107 | 0.0034 | 0.0074 | 0.035 |
| CE18.1n7 | 0.1112 | 0.0508 | 2.1904 | 0.0338 | 0.0089 | 0.2136 |
| CE22.1n9 | 0.0219 | 0.0069 | 3.1675 | 0.0031 | 0.0079 | 0.0359 |
| CE18.2n6 | −2.8632 | 1.4447 | −1.9819 | 0.0535 | −5.7711 | 0.0448 |
| CE20.4n6 | 1.6499 | 0.406 | 4.064 | 2.00E−04 | 0.8327 | 2.4671 |
| CE22.6n3 | 0.1485 | 0.0534 | 2.7798 | 0.0079 | 0.0409 | 0.256 |

Phosphatidylcholine composition changes differed in 18:1n7, 20:3n9, 22:1n9, 20:3n6 and 20:4n6. High responders had greater increases with treatment in 18:1n7 and 22:1n9 and greater decreases in 20:3n6 and 20:4n3. A slight decrease in 20:3n9 occurred with high responders while a significant increase occurred in low responders,

TABLE 3

Estimate and inference of the difference between change in high and low responders in phosphatidylcholine.

| Metabolites | Estimate | ANOVA | | | | |
|---|---|---|---|---|---|---|
| | | Std. Err | T. value | P. value | Lower. CI | Upper. CI |
| PC18.1n7 | 0.2248 | 0.0744 | 3.0208 | 0.0047 | 0.0737 | 0.3759 |
| PC20.3n9 | −0.0509 | 0.0188 | −2.7084 | 0.0106 | −0.0892 | −0.0127 |
| PC22.1n9 | 0.0064 | 0.0033 | 1.9342 | 0.0614 | −3.00E−04 | 0.0132 |
| PC18.2n6 | −1.5254 | 1.278 | −1.1936 | 0.2407 | −4.1199 | 1.0691 |
| PC20.3n6 | −0.468 | 0.2555 | −1.832 | 0.0757 | −0.9872 | 0.0512 |
| PC20.4n6 | 1.1779 | 0.8804 | 1.3379 | 0.1896 | −0.6094 | 2.9651 |
| PC18.3n3 | −0.0498 | 0.027 | −1.8422 | 0.0742 | −0.1047 | 0.0051 |
| PC20.4n3 | −0.0282 | 0.0136 | −2.0734 | 0.0458 | −0.0558 | −6.00E−04 |
| PC22.6n3 | 0.4153 | 0.3249 | 1.2785 | 0.2095 | −0.2442 | 1.0748 |

A few differences were present in diglyceride composition. A larger increase in the concentration of 18:0 in high responders was observed while 18:1n9 and 18:2n6 decreased more in high than low responders. Low responders had a larger increase in DG20:3n9 over high responders.

TABLE 4

Estimate and inference of the difference between change in high and low responders in diglycerides.

| Metabolites | Estimate | ANOVA | | | | |
|---|---|---|---|---|---|---|
| | | Std. Err | T. value | P. value | Lower. CI | Upper. CI |
| DG18.0 | 1.9514 | 0.8297 | 2.3518 | 0.0233 | 0.278 | 3.6247 |
| DG18.1n9 | −3.2461 | 1.4795 | −2.194 | 0.0333 | −6.2242 | −0.268 |
| DG20.3n9 | −0.0911 | 0.0462 | −1.9743 | 0.0546 | −0.1842 | 0.0019 |
| DG18.2n6 | −2.7837 | 1.309 | −2.1266 | 0.0388 | −5.4185 | −0.1489 |

Only two metabolites had different concentrations between high and low responders in the free fatty acid pool. While there was on average no change in the concentration of 20:1n9 and 22:2n6 in low responders, high responders had increased concentrations of 20:1n9 and decreased concentrations of 22:2n6.

TABLE 5

Estimate and inference of the difference between change in high and low responders in free fatty acids.

| Metabolites | ANOVA | | | | | |
|---|---|---|---|---|---|---|
| | Estimate | Std. Err | T. value | P. value | Lower. CI | Upper. CI |
| FA20.0 | 0.0159 | 0.0193 | 0.8242 | 0.4147 | −0.0231 | 0.0549 |
| FA20.1n9 | 0.0823 | 0.0495 | 1.6623 | 0.1034 | −0.0174 | 0.1821 |
| FA22.1n9 | −0.0615 | 0.0421 | −1.4603 | 0.1522 | −0.1468 | 0.0237 |
| FA22.2n6 | −0.0088 | 0.0033 | −2.6795 | 0.0124 | −0.0155 | −0.0021 |

Lysophosphatidylcholine had very few differences between high and low responders. There was no significant change in 18:0 in low responders while high responders had a decrease in this metabolite. 18:3n6 decreased in low responders while it increased in high responders.

TABLE 6

Estimate and inference of the difference between change in high and low responders in lysophosphatidylcholine.

| Metabolites | ANOVA | | | | | |
|---|---|---|---|---|---|---|
| | Estimate | Std. Err | T. value | P. value | Lower. CI | Upper. CI |
| LY16.0 | −1.1505 | 1.0273 | −1.12 | 0.2692 | −3.2251 | 0.9241 |
| LY18.0 | −1.1443 | 0.7618 | −1.5021 | 0.1407 | −2.6827 | 0.3941 |
| LY14.1n5 | 0.0135 | 0.0454 | 0.2986 | 0.7671 | −0.0788 | 0.1059 |
| LY18.1n9 | 0.3099 | 0.5766 | 0.5374 | 0.5939 | −0.8545 | 1.4742 |
| LY18.3n6 | 0.0774 | 0.0259 | 2.9883 | 0.0058 | 0.0243 | 0.1305 |
| LY20.4n6 | 0.1269 | 0.3876 | 0.3275 | 0.7449 | −0.6553 | 0.9092 |
| LY20.4n3 | −0.019 | 0.0122 | −1.5606 | 0.1291 | −0.044 | 0.0059 |
| LY20.5n3 | 0.0994 | 0.0721 | 1.3784 | 0.1755 | −0.0462 | 0.2451 |

Differences in phosphatidylethanolamine included large decreases in 18:0, 18:2n6 and 20:3n6 in the high responders while the low responders had no significant change. There was a subtle difference between high and low responders in the change of 14:1n5, where high responders tended to have increased concentrations after treatment.

TABLE 7

Estimate and inference of the difference between change in high and low responders in phosphatidylethanolamine.

| Metabolites | ANOVA | | | | | |
|---|---|---|---|---|---|---|
| | Estimate | Std. Err | T. value | P. value | Lower. CI | Upper. CI |
| PE18.0 | −2.0267 | 0.8983 | −2.2561 | 0.029 | −3.8359 | −0.2174 |
| PE20.0 | 0.0189 | 0.0166 | 1.1438 | 0.2593 | −0.0145 | 0.0524 |
| PE14.1n5 | 0.0551 | 0.031 | 1.7799 | 0.0833 | −0.0076 | 0.1178 |
| PE18.2n6 | −1.036 | 0.5136 | −2.0172 | 0.0497 | −2.0705 | −0.0016 |
| PE20.3n6 | −0.4196 | 0.103 | −4.0753 | 2.00E−04 | −0.6271 | −0.2121 |
| PE20.4n3 | −0.0102 | 0.007 | −1.4607 | 0.1545 | −0.0245 | 0.0041 |
| PE22.5n3 | −0.1266 | 0.0945 | −1.3399 | 0.1872 | −0.3169 | 0.0638 |

In triglycerides, only 18:4n3 was significantly different between high and low responders. The concentration of this fatty acid increased in the low responders while it did not change significantly in the high responders.

TABLE 8

Estimate and inference of the difference between change in high and low responders in triglyceride.

| Metabolites | ANOVA | | | | | |
|---|---|---|---|---|---|---|
| | Estimate | Std. Err | T. value | P. value | Lower. CI | Upper. CI |
| TG22.0 | 0.0184 | 0.0117 | 1.5774 | 0.1219 | −0.0051 | 0.042 |
| TG20.3n9 | −0.0052 | 0.0247 | −0.2104 | 0.8343 | −0.055 | 0.0446 |
| TG18.3n6 | 0.1008 | 0.0669 | 1.5062 | 0.139 | −0.034 | 0.2356 |
| TG20.4n6 | 0.1005 | 0.1187 | 0.8472 | 0.4015 | −0.1386 | 0.3397 |
| TG22.4n6 | −0.0138 | 0.0163 | −0.8475 | 0.4012 | −0.0466 | 0.019 |
| TG22.5n6 | −0.0165 | 0.0171 | −0.9631 | 0.3406 | −0.0509 | 0.018 |
| TG18.3n3 | −0.0787 | 0.1465 | −0.537 | 0.5939 | −0.3737 | 0.2164 |
| TG18.4n3 | 0.0378 | 0.017 | 2.2198 | 0.0318 | 0.0035 | 0.0721 |
| TG20.4n3 | −0.0056 | 0.0063 | −0.8792 | 0.384 | −0.0184 | 0.0072 |

ANCOVA results. ANCOVA was used to examine the difference between high and low responders after adjusting for baseline concentrations and the time the samples were run. In most cases, the same metabolites that were found to be different from the ANOVA and contrasts were significant in the ANCOVA.

Those fatty acids that were significant (at alpha=0.01) in contrasts of ANOVA, but not after adjusting for baseline and time were CE18:2n6, DG18:0, DG18:1n9, DG20:3n9, DG18:2n6, FA20:1n9, LY18:0, and LY18:3n6. Those fatty acids that were not significant in the contrasts of ANOVA but were significant in the ANCOVA were FA22:2n6, LY20:4n3, PC20:4n6, and PC22:6n3.

Master List of Serum Lipid Metabolites Differentially Affected in High and Low Responders in Response to Simvastatin Treatment. The markers listed here represent those that were significantly affected by treatment with simvastatin. These markers were differentially affected in high and low responders and are the result of additional metabolism affected by statin treatment or by effects secondary to HMG-CoA reductase inhibition. The markers may be used to (1) predict the efficacy of statin treatment provided they respond more quickly than serum cholesterol levels, or (2) identify subjects with additional beneficial or detrimental metabolisms resulting from statin treatment.

Decreased in high responders relative to low responders: CELC, FCLC, PCLC, PELC, DGn6, DG18.1n9, CE18.2n6, DG18.2n6, PE18.0, PE8.2n6, PE20.3n6, DG20.3n9, PC20.3n9, PC20.4n3, FA22.2n6, TGLC, PC18:2n6, PC18:3n3, PC20:3n6, LY18:0, LY20:4n3

Increased in high responders relative to low responders: CE24.0, CE22.1n9, TG18.4n3, LY18.3n6, CE18.1n7, CE18.0, CE22.6n3, PC18.1n7, CE20.4n6, DG18.0, DGSFA, DGLC, PC20:4n6, PC22:1n9, PC22:6n3, TG18:3n6

Example 2

Prediction of Response

Experimental

Statistical Analysis for Prediction of Response. In order to determine if fatty acids at pre-dose were predictive of response to simvastatin, logistic regression was employed using the samples and dataset described in Example 1. The response variable was the dichotomized response and the predictors were baseline LDL cholesterol and the fatty acid. Each fatty acid was evaluated using this model. P-values and odds ratios are reported for each fatty acid.

Linear discriminant analysis was employed to evaluate the performance of sets of metabolites for prediction of response to simvastatin.

Results

Fatty acids with p-values less than 0.1 are included in Table 9. The first column shows the p-values for the covariate, baseline LDL cholesterol. The second column shows the p-value for the fatty acids. The third column shows the lower bound for the estimate of the odds ratio, the fourth column shows the estimate of the odds ratio and the last column shows the upper bound for the estimate of the odds ratio. The relationship of the diglyceride fatty acids 14:0, 16:0, 14:1n5, and 18:1n9 to response are of particular interest. Total saturated fatty acids in diglyceride may be predictive.

Using backward step-wise selection of predictors two combinations of fatty acids were found to predict response. A discriminant composed of CE16:0, CE 20:3n9 and DG18:1n9 classified 34 out of 48 subjects correctly as responders and non-responders. CE16:0, CE20:3n9, and PC18:1n9 correctly classified 33 out of 48 subjects.

TABLE 9

Results of logistic regression analysis with response as outcome and baseline fatty acid measurement as predictor.

| Fatty Acid | LDL pvalue | Fatty Acid pvalue | LB | Odds Ratio | UB |
|---|---|---|---|---|---|
| CE16.0 | 0.1747 | 0.0965 | 0.24 | 0.51 | 1.07 |
| CE20.3n9 | 0.154 | 0.0572 | 0.18 | 0.41 | 0.95 |
| CE22.5n6 | 0.2438 | 0.0999 | 0.22 | 0.51 | 1.16 |
| DG14.0 | 0.0785 | 0.0256 | 0.19 | 0.41 | 0.89 |
| DG16.0 | 0.1772 | 0.0126 | 0.09 | 0.26 | 0.74 |
| DG14.1n5 | 0.2869 | 0.0636 | 0.18 | 0.41 | 0.91 |
| DG18.1n9 | 0.0848 | 0.0651 | 0.89 | 1.76 | 3.48 |
| LY22.1n9 | 0.0646 | 0.0388 | 0.86 | 2.39 | 6.66 |
| LY18.3n6 | 0.2343 | 0.0572 | 0.12 | 0.35 | 0.99 |
| PE24.1n9 | 0.359 | 0.0431 | 0.11 | 0.32 | 0.96 |
| PC20.0 | 0.0719 | 0.0409 | 0.17 | 0.46 | 1.26 |
| PC22.0 | 0.4164 | 0.0151 | 0.13 | 0.33 | 0.84 |
| PC18.1n9 | 0.1416 | 0.0493 | 0.18 | 0.43 | 1.04 |
| TG22.1n9 | 0.097 | 0.0992 | 0.36 | 0.68 | 1.3 |
| TG18.4n3 | 0.0236 | 0.0477 | 0.2 | 0.59 | 1.73 |

SUMMARY: Serum Lipid Metabolites Predictive of High and Low Responders to Simvastatin Treatment. The markers listed here represent those that were predictive of high and low response to simvastatin. The concentration of these markers in fasted, pre-treatment serum or plasma could be used to identify individuals who will benefit greatly or minimally (in terms of LDL-C lowering) in response to statin treatment. It is likely that these markers reflect differences in the rate of LDL metabolism (hydrolysis of lipids, clearance by liver, etc) in blood in subjects that is indicative of the different response to statins. The markers may be used to predict the efficacy of statin treatment in terms of LDL-cholesterol lowering.

Metabolites that when increased predict high response to treatment or when decreased predict a low response to treatment: DG18:1n9, LY22:1n9

Metabolites that when decreased predict high response to treatment or when increased predict a low response to treatment: CE16:0, CE20:3n9, CE22:5n6, DG14:0, DG16:0, DG14:1n5, LY18:3n6, PE24:1n9, PC20:0, PC22:0, PC18:1n9, TG22:1n9, TG18:4n3.

Example 3

Sterols, Phytosterols, Oxysterols, Bile Acids and Bile Acid Conjugates as Predictive and Response Markers The data presented above indicates that structural and energetic lipids can weakly predict the response of individuals to statin treatment, and that these metabolites can identify individuals responding to treatment by the effect of statins on lipid metabolisms not directly related to HMG-CoA reductase inhibition. In particular, one can measure the sterols, phytosterols, oxysterols, bile acids and bile acid conjugates (e.g., from serum) to identify predictive markers of statin response. The role of these metabolites in cholesterol metabolism and cholesterol homeostasis is shown in FIG. 1 and an illustrative but nonlimiting list of these metabolites is provided hereinbelow. Individual differences in cholesterol metabolism and in the way individuals maintain cholesterol homeostasis underpin the response to statin treatment, and these differences are apparent from the panel of markers measured.

TABLE 10

Additional Metabolites.

Bile Acids:

Cholic acid
Chenodeoxycholic acid
Deoxycholic acid
Lithocholic acid
Ursodeoxycholic acid
beta-muricholic acid
Conjugated Bile Acids:

Glycocholic acid
Glycochenodeoxycholic acid
Glycodeoxycholic acid
Glycolithocholic acid
Glycoursodeoxycholic acid
Taurocholic acid
Taurochenodeoxycholic acid
Taurodeoxycholic acid
Taurolithocholic acid
Oxysterols:

4-cholesten-7b-ol-3-one
7α-hydroxycholesterol
Endogenous Sterols:

7-dehydrocholesterol
Cholesterol
Cholestanol
Coprostanol
Desmosterol
Lanosterol
Lathosterol
Phytosterols:

β-sitosterol
Campesterol
Fucosterol
Stigmasterol

Predictive Markers. When the concentrations of the following metabolites are found in blood at levels higher than a normal control population, they predict that a subject will have a positive response to treatment: 4-cholesten-7a-ol-3-one (4-CHST), 7α-hydroxycholesterol (7α-HC), 7-dehydrocholesterol (7-DHC), cholestanol (CSTN), desmosterol (DESM), lanosterol (LANO), lathosterol (LATHO).

When the concentrations of the following metabolites are found in blood at levels higher than a normal control population, they predict that a subject will have a negative response to treatment: β-sitosterol (β-SITO), campesterol (CAMP), stigmasterol (STIG), coprostanol (COPR).

Response Markers. When the concentrations of the following metabolites are found to increase in blood after treatment with a statin, they predict that a subject will have a negative response to treatment: β-sitosterol (β-SITO), campesterol (CAMP), stigmasterol (STIG), coprostanol (COPR), 7-dehydrocholesterol (7-DHC), cholestanol (CSTN), desmosterol (DESM), lanosterol (LANO), lathosterol (LATHO). If these same metabolites are found to decrease in blood after treatment, they indicate a positive response to treatment.

When the concentrations of the following metabolites are found to decrease in blood after treatment with a statin, they predict that a subject will have a negative response to treatment: 4-cholesten-7a-ol-3-one (4-CHST), 7α-hydroxycholesterol (7α-HC). If these same metabolites are found to increase in blood after treatment, they indicate a positive response to treatment.

We evaluated lipid profiles of 48 subjects selected from the Pharmacogenetics and Risk of Cardiovascular Disease (PARC) study. Subjects were selected from the larger study population of 944 participants (335 African-Americans and 609 whites), with a baseline total serum cholesterol level of 160 to 400 mg/dl. Participants were followed for a total of 6 weeks on simvastatin therapy (40 mg at bedtime). Twenty-four subjects drawn from the top 10% of responders and 24 age-, gender-, and race-matched subjects from the bottom 10% of responders. Response was defined as percent change in LDL cholesterol from baseline to end of treatment. Samples used in this study were collected at baseline and at 6 weeks of therapy.

Experimental

Data Reporting. Lipids measured included: cholesterol, lanosterol, lathosterol, cholestanol, 7-dehydrocholesterol, β-sitosterol, campesterol, desmosterol, stigmasterol, 7α-hydroxycholesterol, 4-cholesten-7α-ol-3-one, cholic acid, chenodeoxycholic acid, deoxycholic acid, lithocholic acid, ursodeoxycholic acid, glycocholic acid, taurocholic acid, glycodeoxycholic acid, taurodeoxycholic acid, glycodeoxycholic acid, taurodeoxycholic acid, glycolithocholic acid, taurolithocholic acid, and/or glycoursodeoxycholic acid.

Sterols, Phytosterol and Oxysterol Quantification Method. To 50 μL of plasma or serum in a microtube was added 10 μL of a mixture of dueterated surrogates for quantitation. Ethanolic potassium hydroxide (250 μL 1M) was added to the sample. The microtube was purged with nitrogen, capped and vortexed for 30 seconds. The sample was then incubated at 70° C. for 1 hour. The sample was cooled in a refrigerator for 15 minutes and then 250 μL deionized water was added. The free sterols were then extracted with two 500 μL volumes of hexane:ethanol (20:1). The combined hexane layers were transferred to a GC vial, dried down under nitrogen and reconstituted in 50 μL decane. 30 μL Tri-Sil derivatizing reagent was added to the sample which was then vortexed for 10 seconds. Finally, silylated sterols were injected onto an 6890/5975 GC/MS (Agilent Technologies, CA) with an 30 m×0.25 mm Rxi-5 ms column (Restek, PA) with helium as the carrier gas. Mass spectrometric analysis was performed in the single ion monitoring (SIM) mode with electron ionization.

Bile Acid Quantification Method. The bile acids from 150 μL of plasma or serum were extracted using protein precipitation and filtering. Ten microliters of a mixture of deuterated surrogates for quantitation was then added to each sample and thoroughly vortexed. Protein precipitation was carried out by adding 800 μl of acetonitrile to each sample followed by vortexing. The samples were centrifuged at −4° C. and 17000 g for 10 minutes. The supernatants were dried under nitrogen for 1 hour at 10 psi. Dried samples were reconstituted with 60 μl methanol:deionized water (50:50). After vortexing, samples were transferred to silanized autosampler inserts for LC/MSMS analysis. The samples were injected onto an Agilent Stable Bond C18 reverse phase column (150×2.1 mm, 1.8 micron) connected to a Applied Biosystems 4000 QTRAP. The analytes were ionized via negative electrospray and the mass spectrometer was operated in the tandem MS mode.

Statistical Methods. Before undertaking analysis, the data was cleaned by outlier removal and removal of uninformative metabolites. Outliers were identifies as those observation more than three standard deviations from the mean. Metabolites were determined to be uninformative if over ⅔rds of the observations were below the limit of detection and the pattern of observations falling below this limit was not related to the outcome.

Results

Study Analysis 1: Prediction of Simvastatin Response from Baseline Samples

Figure 3:
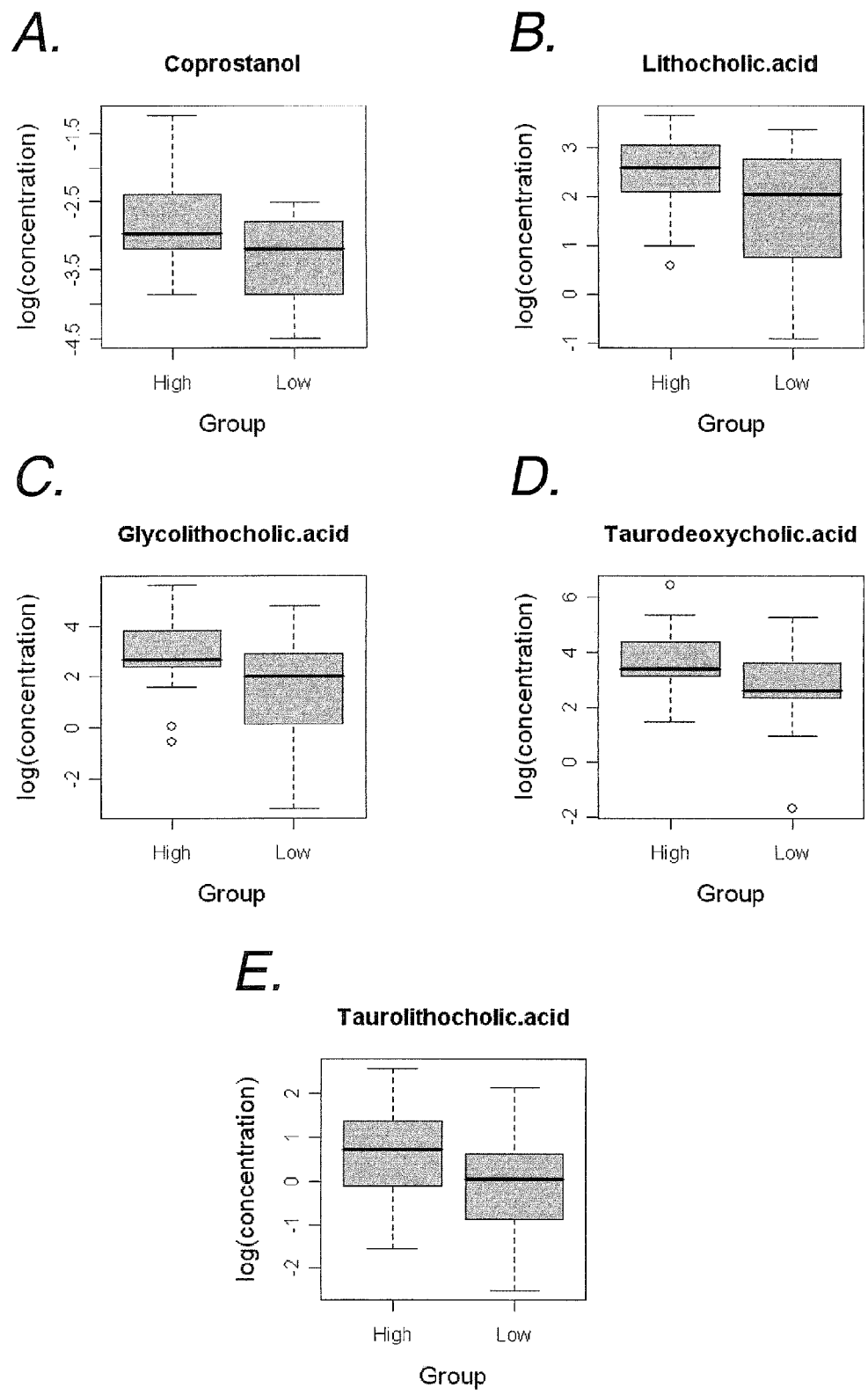
FIG. 3. Box plot of the log transformed concentration of metabolites. (A) Coprostanol; (B) Lithocholic acid; (C) Glycolithocholic acid; and (D) Taurodeoxycholic acid; (E) Taurolitocholic acid.

This study consisted of 22 low responders and 23 high responders to simvastatin treatment as assessed by the degree of LDL-C lowering after 6 weeks of treatment. Our interest was in determining if an association existed between pre-dose measurements and whether the subjects were high or low responders. We used a logistic regression to determine if a relationship existed between pre-dose concentrations of bile acids and sterols and response to simvastatin. The data were log transformed due to long right tails. Odds ratios and confidence intervals were calculated to assess the significance of the associations (Table 11). Box plots of those metabolites whose odds ratio confidence interval did not include one are included below (FIG. 3).

TABLE 11

Estimates of Odds Ratios from Logistic Regression

| Metabolites | Lower Bound | Odds Ratio | Upper Bound |
| --- | --- | --- | --- |
| Lithocholic acid | 1.20 | 3.04 | 7.70 |
| Taurolithocholic acid | 1.12 | 2.84 | 7.20 |
| Taurodeoxycholic acid | 1.08 | 2.78 | 7.14 |
| Coprostanol | 1.13 | 2.30 | 4.67 |
| Glycolithocholic acid | 1.13 | 2.18 | 4.20 |
| Glycodeoxycholic acid | 0.87 | 1.59 | 2.90 |
| Taurocholic acid | 0.56 | 1.50 | 3.99 |
| Cholesterol | 0.57 | 1.36 | 3.24 |
| Deoxycholic acid | 0.71 | 1.36 | 2.59 |
| Desmosterol | 0.66 | 1.21 | 2.21 |
| 7a-Hydroxycholesterol | 0.57 | 1.19 | 2.47 |
| b-sitosterol | 0.49 | 1.16 | 2.77 |
| Glycoursodeoxycholic acid | 0.46 | 1.15 | 2.85 |
| Taurochenodeoxycholic acid | 0.54 | 1.10 | 2.23 |
| Lathosterol | 0.57 | 1.05 | 1.93 |
| Glycocholic acid | 0.49 | 1.03 | 2.19 |
| 7-Dehydrocholesterol | 0.63 | 1.02 | 1.66 |
| Cholestanol | 0.41 | 1.00 | 2.46 |
| Campesterol | 0.48 | 0.96 | 1.91 |
| Glycochenodeoxycholic acid | 0.44 | 0.91 | 1.88 |
| Ursodeoxycholic acid | 0.40 | 0.90 | 2.02 |
| Stigmasterol | 0.33 | 0.87 | 2.32 |
| Lanosterol | 0.41 | 0.83 | 1.69 |
| Cholic acid | 0.28 | 0.61 | 1.34 |
| Chenodeoxycholic acid | 0.19 | 0.45 | 1.07 |

All those metabolites with significant associations had positive associations (lower bound was >1.0). That is, high responders were more likely to have higher pre-dose concentrations of coprostanol, lithocholic acid, glycolithocholic acid, taurodeoxycholic acid, and taurolithocholic acid than low responders.

These and other sterol metabolites can be used to develop risk scores and diagnostic classifications for statin response from a larger trial.

Interpretation of the Underlying Biochemistry

Figure 2:
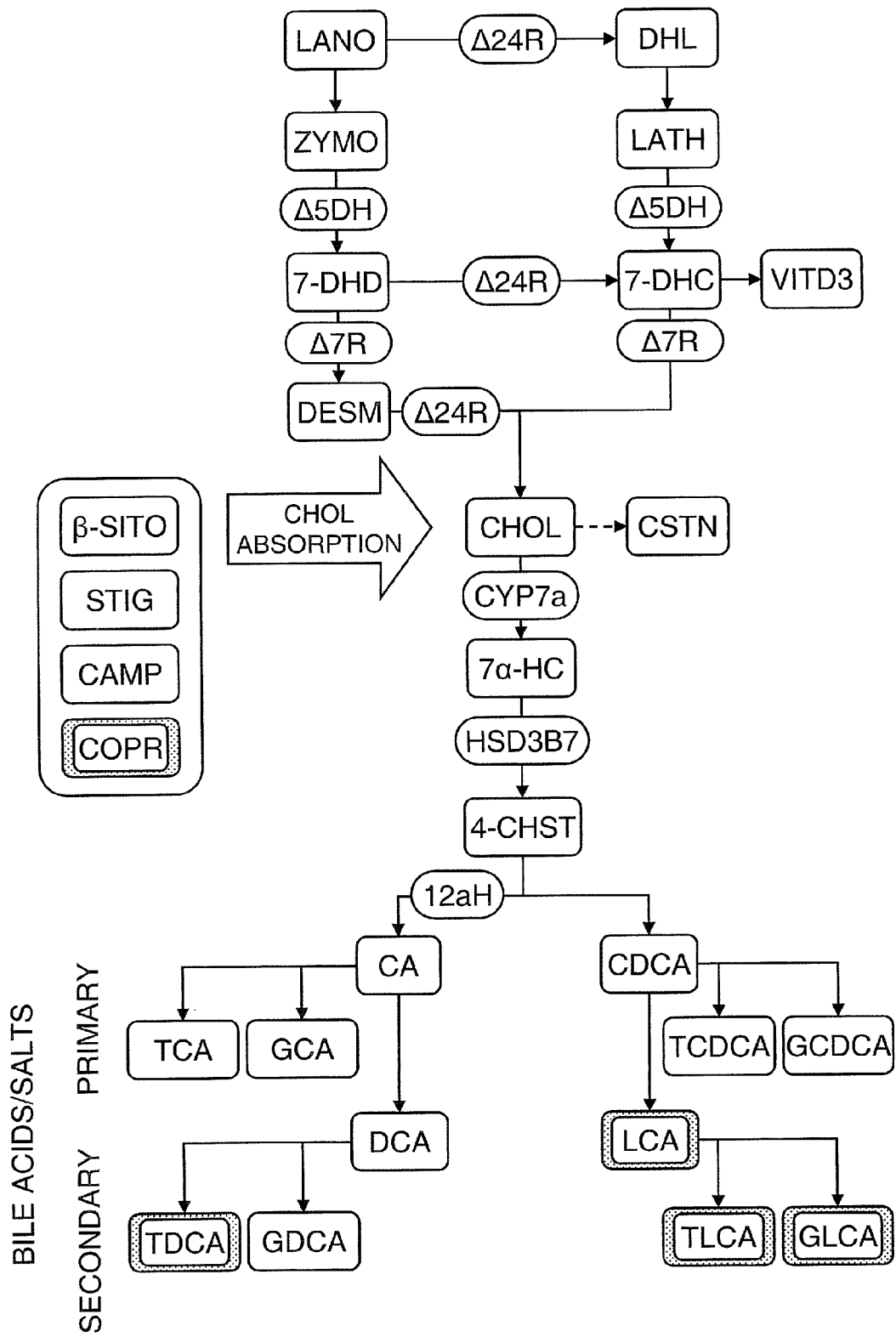
FIG. 2. Cholesterol metabolism in humans. Metabolites positively correlated with statin response are shown in boxes highlighted with stippled borders. Abbreviations: "Vit3D", vitamin D31; HSD3B7, 3 beta-hydroxy-delta 5-C27-steroid oxidoreductase.

The metabolites measured in this experiment comprised those involved in cholesterol synthesis pathways, cholesterol absorption and cholesterol excretion as bile acids and bile salts (FIG. 2).

Coprostanol is a metabolic product of cholesterol produced only by intestinal microflora. It is poorly absorbed relative to cholesterol, phytosterols and bile acids, but the presence of this analyte in serum is unequivocally the result of: cholesterol excretion in bile→conversion to coprostanol by microflora→reabsorption by enterocytes.

The bile acids and salts identified as predictive markers of statin response were all secondary products, meaning that like coprostanol they were produced by bacterial metabolism of endogenous bile salts in the intestine. Thus, these metabolites by definition were absorbed through entero-hepatic recirculation.

All five independently quantified metabolites in Table 11 predictive of statin response were intestinal bacterial products of endogenous cholesterol or bile acids.

Metabolite Ratios Reflecting Cholesterol Synthesis, Absorption and Degradation Pathways Cholesterol synthesis can be divided into two pathways (FIG. 2). Our hypothesis was that each pathway would be differentially affected by simvastatin treatment. Since each pathway is affected differently, then measures of flux through each pathway provide insight into which subjects respond to simvastatin treatment. Such metabolite ratios can be determined prior to treatment to predict which subjects will have a positive or negative response to simvastatin treatment and/or can be measured after treatment has started to determine which subjects are having a positive or negative to simvastatin treatment. Nonlimiting examples of ratios include:

Synthetic pathway 1: Ratio of desmosterol/lanosterol
Synthetic pathway 2: Ratio of lathosterol/lanosterol
Synthetic pathway 2 (version 2): lathosterol+7-dehydrocholesterol/lanosterol Other ratios based on cholesterol synthetic pathways that correlate with response to simvastatin (at baseline and/or after treatment commences) include:

Ratio of 7-dehydrocholesterol/cholesterol
Ratio of cholestanol/cholesterol
Ratio of desmosterol/cholesterol
Ratio of lanosterol/cholesterol
Ratio of lathosterol/cholesterol A relatively high value for these ratios in pre-treatment samples indicates that the subject will have a positive response to simvastatin treatment, and a relatively high ratio in post-treatment samples indicates that the subject is having a negative response to treatment.

Cholesterol absorption is negatively correlated with simvastatin response and can be evaluated by looking at metabolite ratios at baseline and/or after treatment commences. Nonlimiting examples of such ratios include.

Ratio of β-sitosterol/cholesterol
Ratio of campesterol/cholesterol
Ratio of fucosterol/cholesterol
Ratio of stigmasterol/cholesterol
Ratio of coprostanol/cholesterol A relatively high value of these ratios pre-treatment indicates that the subject will have a positive response to simvastatin treatment, and a relatively high ratio post-treatment indicates that the subject is having a positive response to simvastatin treatment.

Cholesterol degradation pathways can also be used to evaluate responsiveness (at baseline and/or after treatment commences) to statins. Nonlimiting examples of metabolite ratios relevant to cholesterol degradation include:

Ratio of any bile acid such as cholic acid/cholesterol
Ratio of primary bile acids/cholesterol
Ratio of secondary bile acids/cholesterol In addition, the ratio of secondary bile acids/primary bile acids can be used to predict or to evaluate response (e.g., at baseline and/or after treatment commences) to statins. Relatively low ratios of secondary bile acid(s)/primary bile acid(s) prior to treatment indicate a positive response to simvastatin treatment and/or relatively high ratios post-treatment indicate a positive response to simvastatin treatment. Illustrations of such ratios include:

Ratio of secondary bile acids/primary bile acids; and/or
Ratio of one or more secondary bile acids/one or more primary bile acids Study Analysis 2: Response to Treatment Of secondary interest was how the bile acids and sterols responded to statin treatment and if they were differentially affected in responders and non-responders. We used an ANCOVA to investigate both of these questions. The model included the baseline concentration of the metabolite as a covariate and response category was included as a factor. The outcome was the change from pre-treatment to post-treatment. Table 12 includes the results from this analysis as well as paired t-tests on pre to post concentrations.

Key Findings

Cholesterol, 7-dehydrocholesterol, coprostanol and desmosterol were all significantly reduced in the responders, while unchanged in the non-responders. The effects in high responders were strong and consistent.

Lanosterol was significantly depleted by a similar magnitude in both responders and non-responders.

Lathosterol was extremely noisy and the direction of the change is questionable. Further studies have indicated that lathosterol decreases more substantially post-treatment in subjects who are good responders.

Bile acids, oxysterols and phytosterols did not change in a consistent or meaningful manner.

TABLE 12

Results of ANCOVA and Paired t-tests

| Metabolites | Low-Response | P-Value | High-Response | P-Value |
|---|---|---|---|---|
| Cholesterol | Unchanged | 0.20 | Decreased | <0.01 |
| Lanosterol | Decreased | <0.01 | Decreased | <0.01 |
| 7-Dehydrocholesterol | Unchanged | 0.10 | Decreased | 0.03 |
| Desmosterol | Unchanged | 0.16 | Decreased | 0.02 |
| Coprostanol | Unchanged | 0.51 | Decreased | <0.01 |

The p-value for the Responder indicates if the metabolite was affected differently in high versus low responders. The p-values from the t-tests are broken down by LOW responders and HIGH responders.

Summary

Serum Lipid Metabolites Predictive of High and Low Responders to Simvastatin Treatment. The markers listed here represent those that were predictive of high and low response to simvastatin prior to treatment. The concentration of these markers in fasted, pre-treatment serum or plasma could be used to identify individuals who will benefit (e.g., in terms of LDL-cholesterol lowering) in response to statin treatment. It is likely that these markers reflect differences in the rate of LDL metabolism (hydrolysis of lipids, clearance by liver, etc) in blood in subjects that is indicative of the different response to statins. The markers may be used to predict the efficacy of statin treatment (e.g., in terms of LDL-cholesterol lowering).

Metabolites that when increased in pre-treatment samples predict high response to treatment or when decreased predict a low response to treatment: lithocholic acid, taurolithocholic acid, taurodeoxycholic acid, coprostanol, glycolithocholic acid, glycodeoxycholic acid, and deoxycholic acid Metabolites that when decreased in pre-treatment samples predict high response to treatment or when increased predict a low response to treatment: cholic acid, and chenodeoxycholic acid.

Metabolites that when decreased in post-treatment samples indicate good response or when increased or show no change in post-treatment samples indicate a poor response to treatment: cholesterol, 7-dehydrocholesterol, coprostanol and desmosterol.

Example 4

Eicosanoids as Predictive and Response Markers

Inflammation and inflammatory processes are associated with the development and progression of cardiovascular disease. Drugs which alter the synthesis of eicosanoids are used to treat CVD (Levick S P, Loch D C, Taylor S M, Janicki J S., *J Immunol* 2007 Jan. 15; 178(2):641-6). Analysis of eicosanoids as set forth in Table 13 below provide additional predictive information for the prediction of the response to statin therapy.

TABLE 13

Eicosanoids.

| Cyclooxygenase Products | Lipoxygenase Products | Cytochrome P450 Products | Oxidative Stress Markers |
|---|---|---|---|
| Prostaglandin E2 | Leukotriene B4 | 20-HETE | 9-HODE |
| 13,14-dihydro-15-keto PGA2 | Leukotriene B5 | 9,10-DiHOME | 13-HODE |
| Prostaglandin B2 | Leukotriene C4 | 12(13)-DiHOME | 8-iso-PGF2a |
| Prostaglandin F2a | Leukotriene D4 | 8(9)-EpETrE | |
| 15-keto Prostaglandin F2a | Leukotriene E4 | 11(12)-EpETrE | |
| 6-keto Prostaglandin F1a | Leukotriene F4 | 8,9-DiHETrE | |
| Thromboxane B2 | 5-HETE | 14(15)-EpETrE | |
| 11-dehydro Thromboxane B2 | 5(S)-HEPE | 5,6-DiHETrE | |
| Prostaglandin D2 | 8-HETE | 5(6)-EpETrE | |
| 11b-Prostaglandin F2a | 9-HETE | 12(13)-EpOME | |
| Prostaglandin J2 | 11-HETE | 9(10)-EpOME | |
| 15-deoxy-12,14-Prostaglandin J2 | 12-HETE | 17,18-DiHETE | |
| | 12(S)-HEPE | 19,20-DiHDPA | |
| | 15-HETE | 14,15-DiHETE | |
| | 15(S)-HEPE | 14,15-DiHETrE | |
| | Lipoxin A4 | 11,12-DiHETrE | |
| | | 19(20)-EpDPE | |
| | | 17(18)-EpETE | |
| | | 14(15)-EpETE | |

The foregoing is illustrative of the present invention, and is not to be construed as limiting thereof. The invention is defined by the following claims, with equivalents of the claims to be included therein.

That which is claimed is:

1. A method of correlating a lipid profile with a positive or negative response to a statin treatment regimen, the method comprising:
   determining a lipid profile of a sample obtained from a mammalian subject following commencement of the treatment regimen and before the positive or negative response can be detected; and
   correlating the lipid profile in the sample with a positive or negative response to the treatment regimen;
   wherein the positive response to treatment comprises one or more of a reduction in the level of total cholesterol, a reduction in the level of low density lipoprotein (LDL) cholesterol, a reduction in the level of high density lipoprotein (HDL) cholesterol and a reduction in the level of total triglyceride detected in the sample obtained following commencement of the treatment regimen as compared with the level prior to commencing the treatment regimen.

2. The method of claim 1, wherein the subject is afflicted with or at risk for a cardiovascular disorder (CVD), and the treatment regimen is to treat or prevent said CVD.

3. The method of claim 1, wherein the method comprises detecting one or more ratios between lipid metabolites in a pathway.

4. The method of claim 1, wherein the lipid profile evaluates lipid metabolites in two or more lipid classes.

5. The method of claim 1, wherein the lipid profile evaluates two or more lipid metabolites within one or more lipid classes.

6. The method of claim 1, wherein the method comprises detecting an amount of a lipid metabolite.

7. The method of claim 1, wherein the method comprises detecting a mole % within class of a lipid metabolite.

8. The method of claim 1, wherein said lipid profile comprises at least two lipid metabolites selected from the group consisting of: triglycerides, free fatty acids, diacylglycerols, fatty-acid derived phospholipids, sphingolipids, glycolipids, terpenoids, cholesterol esters, steroids, bile acids, oxysterols, endogenous sterols, phytosterols, and eicosanoids.

9. The method of claim 1, wherein said lipid profile comprises at least one lipid metabolite from the primary bile acid and/or secondary bile acid class.

10. The method of claim 9, wherein said primary and/or secondary bile acid comprises taurodeoxycholic acid, taurocholic acid, glycocholic acid, glycoursodeoxycholic acid, lithocholic acid, taurolithocholic acid, glycolithocholic acid, taurochenodeoxycholic acid and/or glycochenodeoxycholic acid.

11. The method of claim 1, wherein:
    said lipid profile includes at least one lipid metabolite; and
    wherein a decrease in said at least one lipid metabolite in said sample from said subject as compared with a sample from said subject prior to commencement of said statin treatment regimen indicates a positive response by said subject to said treatment regimen,
    said at least one lipid metabolite selected from the group consisting of CELC, FCLC, PCLC, PELC, DGn6, DG18.1n9, CE18.2n6, DG18.2n6, PE18.0, PE18.2n6, PE20.3n6, DG20.3n9, PC20.3n9, PC20.4n3, FA22.2n6, TGLC, PC18:2n6, PC18:3n3, PC20:3n6, LY18:0, and LY20:4n3.

12. The method of claim 1, wherein:
    said lipid profile includes at least one lipid metabolite; and
    wherein an increase in said at least one lipid metabolite in said sample from said subject as compared with a sample from said subject prior to commencement of said treatment regimen indicates a positive response by said subject to said statin treatment regimen,
    said at least one lipid metabolite selected from the group consisting of CE24.0, CE22.1n9, TG18.4n3, LY18.3n6, CE18.1n7, CE18.0, CE22.6n3, PC18.1n7, CE20.4n6, DG18.0, DGSFA, DGLC, PC20:4n6, PC22:1n9, PC22: 6n3, and TG18:3n6.

13. The method of claim 1, wherein:
    said lipid profile includes at least one lipid metabolite; and
    wherein an increase in said at least one lipid metabolite in said sample from said subject as compared with a sample from said subject prior to commencement of said statin treatment regimen indicates a positive response by said subject to said treatment regimen,
    said at least one lipid metabolite selected from the group consisting of: 4-cholesten-7a-ol-3-one and 7α-hydroxy-cholesterol.

14. The method of claim 1, wherein:
    said lipid profile includes at least one lipid metabolite; and
    wherein a decrease in said at least one lipid metabolite in said sample from said subject as compared with a sample from said subject prior to commencement of said statin treatment regimen indicates a positive response by said subject to said treatment regimen,
    said at least one lipid metabolite selected from the group consisting of: lanosterol, 7-dehydrocholesterol, coprostanol, and desmosterol.

15. The method of claim 1, wherein:
said lipid profile includes at least one lipid metabolite; and
wherein a decrease in said at least one lipid metabolite in said sample from said subject as compared with a sample from said subject prior to commencement of said statin treatment regimen indicates a positive response by said subject to said treatment regimen,
said at least one lipid metabolite selected from the group consisting of: β-sitosterol, campesterol, stigmasterol, coprostanol, 7-dehydrocholesterol, cholestanol, desmosterol, lanosterol, and lathosterol.

16. The method of claim 1, further comprising, when a positive response is correlated to said lipid profile, continuing said treatment regimen in said subject.

17. The method of claim 1, further comprising, when a negative response to said treatment regimen is correlated to said lipid profile, discontinuing said treatment regimen and then commencing a different statin treatment regimen in said subject.

18. The method of claim 17, wherein said different statin treatment regimen comprises: altering the dose of said statin treatment regimen, administering a different statin to said subject, administering an additional active agent to said subject in combination with said statin, or a combination thereof.

19. The method of claim 1, wherein said sample comprises a blood, plasma or serum sample.

20. The method of claim 1, wherein said subject is a human subject.

21. The method of claim 1, wherein said statin treatment regimen is a simvastatin treatment regimen.

22. The method of claim 1, wherein the lipid profile comprises evaluating the presence of at least one lipid metabolite above or below a particular threshold value.

23. The method of claim 1, wherein the sample is taken from the subject within two weeks of starting the statin treatment regimen.

24. The method of claim 1, wherein the sample is taken from the subject within one week of starting the statin treatment regimen.

25. A method of correlating a lipid profile with a positive or negative response to a statin treatment regimen, the method comprising:
determining a lipid profile of a sample obtained from a mammalian subject before commencement of said treatment regimen; and
correlating the lipid profile in the sample with a positive or negative response to said treatment regimen;
wherein the positive response to treatment comprises one or more of a reduction in the level of total cholesterol, a reduction in the level of low density lipoprotein (LDL) cholesterol, a reduction in the level of high density lipoprotein (HDL) cholesterol and a reduction in the level of total triglyceride measured in a sample obtained following commencement of the treatment regimen as compared with the level prior to commencing said treatment regimen.

26. The method of claim 25, wherein said subject is afflicted with or at risk for a cardiovascular disorder (CVD), and said treatment regimen is for said CVD.

27. The method of claim 25, wherein said lipid profile comprises at least two lipid metabolites selected from the group consisting of: triglycerides, free fatty acids, diacylglycerols, fatty-acid derived phospholipids, sphingolipids, glycolipids, terpenoids, cholesterol esters, steroids, bile acids, oxysterols, endogenous sterols, phytosterols, and eicosanoids.

28. The method of claim 25, wherein
said lipid profile includes at least one lipid metabolite; and
wherein an increased level of said metabolite in said sample from said subject as compared with a predetermined standard based on the level of the metabolite in a control population indicates a positive response to said statin treatment regimen; and
wherein a decreased level of said metabolite in a sample from said subject as compared with the predetermined standard indicates a negative response to said statin treatment regimen;
said at least one metabolite selected from the group consisting of: DG18:1n9 and LY22:1n9.

29. The method of claim 25, wherein:
said lipid profile includes at least one lipid metabolite; and
wherein a decreased level of said metabolite in said sample from said subject as compared with a predetermined standard based on the level of the metabolite in a control population indicates a positive response to said statin treatment regimen; and
wherein an increased level of said metabolite in a sample from said subject as compared with the predetermined standard indicates a negative response to said statin treatment regimen,
said at least one metabolite selected from the group consisting of: CE16:0, CE20:3n9, CE22:5n6, DG14:0, DG16:0, DG14:1n5, LY18:3n6, PE24:1n9, PC20:0, PC22:0, PC18:1n9, TG22:1n9, and TG18:4n3.

30. The method of claim 25, wherein
said lipid profile includes at least one lipid metabolite; and
wherein an increased level of said metabolite in said sample from said subject as compared with a predetermined standard based on the level of the metabolite in a control population indicates a positive response to said statin treatment regimen; and
wherein a decreased level of said metabolite in a sample from said subject as compared with the predetermined standard indicates a negative response to said statin treatment regimen;
said at least one metabolite selected from the group consisting of: lithocholic acid, taurolithocholic acid, taurodeoxycholic acid, coprostanol, glycolithocholic acid, glycodeoxycholic acid, and deoxycholic acid.

31. The method of claim 25, wherein
said lipid profile includes at least one lipid metabolite; and
wherein an increased level of said metabolite in said sample from said subject as compared with a predetermined standard based on the level of the metabolite in a control population indicates a positive response to said statin treatment regimen; and
wherein a decreased level of said metabolite in a sample from said subject as compared with the predetermined standard indicates a negative response to said statin treatment regimen;
said at least one metabolite selected from the group consisting of: 4-cholesten-7a-ol-3-one, 7α-hydroxycholesterol, 7-dehydrocholesterol, cholestanol, desmosterol, lanosterol, and lathosterol.

32. The method of claim 25, wherein:
said lipid profile includes at least one lipid metabolite; and
wherein a decreased level of said metabolite in said sample from said subject as compared with a predetermined standard based on the level of the metabolite in a control population indicates a positive response to said statin treatment regimen; and
wherein an increased level of said metabolite in a sample from said subject as compared with the predetermined standard indicates a negative response to said statin treatment regimen,
said at least one metabolite selected from the group consisting of: cholic acid and chenodeoxycholic acid.

33. The method of claim 25, wherein:
said lipid profile includes at least one lipid metabolite; and
wherein a decreased level of said metabolite in said sample from said subject as compared with a predetermined standard based on the level of the metabolite in a control population indicates a positive response to said statin treatment regimen; and
wherein an increased level of said metabolite in a sample from said subject as compared with the predetermined standard indicates a negative response to said statin treatment regimen,
said at least one metabolite selected from the group consisting of: β-sitosterol, campesterol, stigmasterol, and coprostanol.

34. The method of claim 25, wherein said sample comprises a blood, plasma or serum sample.

35. The method of claim 25, wherein said subject is a human subject.

36. The method of claim 1, wherein said lipid profile comprises at least one lipid metabolite that is a plasmalogen-linked fatty acid.

37. The method of claim 1, wherein said lipid profile comprises at least one lipid metabolite that comprises a n3 and/or n6 fatty acid moiety.

38. The method of claim 37, wherein said at least one lipid metabolite is a phospholipid selected from the group consisting of phosphatidylcholine, lysophosphatidylcholine, phosphatidylethanolamine, phosphatidylserine and phosphatidylinositol, wherein the phospholipid comprises the n3 and/or n6 fatty acid moiety.

39. The method of claim 1, wherein said lipid profile comprises at least one lipid metabolite comprising a fatty acid moiety selected from the group consisting of 18:3n3, 20:5n3, 22:6n3, 18:2n6, 18:3n6, 20:3n6, 20:4n6 and 22:5n6.

40. The method of claim 39, wherein said at least one lipid metabolite is selected from the group consisting of CE18:3n3, CE20:5n3, CE22:6n3, CE18:2n6, CE18:3n6, CE20:3n6, CE20:4n6, CE22:5n6, PC18:3n3, PC20:5n3, PC22:6n3, PC18:2n6, PC18:3n6, PC20:3n6, PC20:4n6, PC22:5n6, PE18:3n3, PE20:5n3, PE22:6n3, PE18:2n6, PE18:3n6, PE20:3n6, PE20:4n6, PE22:5n6, TG18:3n3, TG20:5n3, TG22:6n3, TG18:2n6, TG18:3n6, TG20:3n6, TG20:4n6 and TG22:5n6.

41. The method of claim 25, wherein the method comprises detecting one or more ratios between lipid metabolites in a pathway.

42. The method of claim 25, wherein the lipid profile evaluates lipid metabolites in two or more lipid classes.

43. The method of claim 25, wherein the lipid profile evaluates two or more lipid metabolites within one or more lipid classes.

44. The method of claim 25, wherein the method comprises detecting an amount of a lipid metabolite.

45. The method of claim 25, wherein the method comprises detecting a mole % within class of a lipid metabolite.

46. The method of claim 25, wherein said lipid profile comprises at least one lipid metabolite from the primary bile acid and/or secondary bile acid class.

47. The method of claim 46, wherein said primary and/or secondary bile acid comprises taurodeoxycholic acid, taurocholic acid, glycocholic acid, glycoursodeoxycholic acid, lithocholic acid, taurolithocholic acid, glycolithocholic acid, taurochenodeoxycholic acid and/or glycochenodeoxycholic acid.

48. The method of claim 25, wherein the lipid profile comprises evaluating the presence of at least one lipid metabolite above or below a particular threshold value.

49. The method of claim 25, wherein said lipid profile comprises at least one lipid metabolite that is a plasmalogen-linked fatty acid.

50. The method of claim 25, wherein said lipid profile comprises at least one lipid metabolite that comprises a n3 and/or n6 fatty acid moiety.

51. The method of claim 50, wherein said at least one lipid metabolite is a phospholipid selected from the group consisting of phosphatidylcholine, lysophosphatidylcholine, phosphatidylethanolamine, phosphatidylserine and phosphatidylinositol, wherein the phospholipid comprises the n3 and n6 fatty acid moiety.

52. The method of claim 25, wherein said lipid profile comprises at least one lipid metabolite comprising a fatty acid moiety selected from the group consisting of 18:3n3, 20:5n3, 22:6n3, 18:2n6, 18:3n6, 20:3n6, 20:4n6 and 22:5n6.

53. The method of claim 52, wherein said at least one lipid metabolite is selected from the group consisting of CE18:3n3, CE20:5n3, CE22:6n3, CE18:2n6, CE18:3n6, CE20:3n6, CE20:4n6, CE22:5n6, PC18:3n3, PC20:5n3, PC22:6n3, PC18:2n6, PC18:3n6, PC20:3n6, PC20:4n6, PC22:5n6, PE18:3n3, PE20:5n3, PE22:6n3, PE18:2n6, PE18:3n6, PE20:3n6, PE20:4n6, PE22:5n6, TG18:3n3, TG20:5n3, TG22:6n3, TG18:2n6, TG18:3n6, TG20:3n6, TG20:4n6 and TG22:5n6.

54. A method of correlating a lipid profile with a positive or negative response to a statin treatment regimen, the method comprising:
determining a lipid profile of a sample obtained from a mammalian subject following commencement of the treatment regimen; and
correlating the lipid profile in the sample with a positive or negative response to the treatment regimen;
wherein the lipid profile evaluates 10 or more lipid metabolites within one or more lipid classes; and
wherein the positive response to treatment comprises one or more of a reduction in the level of total cholesterol, a reduction in the level of low density lipoprotein (LDL) cholesterol, a reduction in the level of high density lipoprotein (HDL) cholesterol and a reduction in the level of total triglyceride detected in the sample obtained following commencement of the treatment regimen as compared with the level prior to commencing the treatment regimen.

55. The method of claim 54, wherein the lipid profile evaluates 50 or more lipid metabolites within one or more lipid classes.

56. The method of claim 54, wherein the lipid profile evaluates lipid metabolites in three or more lipid classes.

57. A method of correlating a lipid profile with a positive or negative response to a statin treatment regimen, the method comprising:
obtaining a lipid profile of a sample from a mammalian subject before commencement of said treatment regimen; and
correlating the lipid profile in the sample with a positive or negative response to said treatment regimen;
wherein the lipid profile evaluates 10 or more lipid metabolites within one or more lipid classes; and wherein the positive response to treatment comprises one or more of a reduction in the level of total cholesterol, a reduction in the level of low density lipoprotein (LDL) cholesterol, a reduction in the level of high density lipoprotein (HDL) cholesterol and a reduction in the level of total triglyceride detected in a sample obtained following commencement of the treatment regimen as compared with the level prior to commencing said treatment regimen.

58. The method of claim 57, wherein the lipid profile evaluates 50 or more lipid metabolites within one or more lipid classes.

59. The method of claim 57, wherein the lipid profile evaluates lipid metabolites in three or more lipid classes.

* * * * *

UNITED STATES PATENT AND TRADEMARK OFFICE
CERTIFICATE OF CORRECTION

PATENT NO. : 8,137,977 B2
APPLICATION NO. : 12/257957
DATED : March 20, 2012
INVENTOR(S) : Kaddurah-Daouk et al.

It is certified that error appears in the above-identified patent and that said Letters Patent is hereby corrected as shown below:

On Title Page:
Item (56) References Cited, Other Publications, Page 3, Right Column,
    Line 19, Riséet al.: Please correct "Riséet al., Δ5" to read -- Risé et al., Δ5 --
    Line 22, Riséet al.: Please correct "Riséet al." to read -- Risé et al. --
    Line 25, Riséet al.: Please correct "Riséet al." to read -- Risé et al. --

In the Specifications:
Column 17, Line 8: Please correct "flee fatty acids," to read -- free fatty acids, --

Signed and Sealed this
Twenty-fourth Day of July, 2012

David J. Kappos
*Director of the United States Patent and Trademark Office*

UNITED STATES PATENT AND TRADEMARK OFFICE
CERTIFICATE OF CORRECTION

PATENT NO. : 8,137,977 B2
APPLICATION NO. : 12/257957
DATED : March 20, 2012
INVENTOR(S) : Kaddurah-Daouk et al.

It is certified that error appears in the above-identified patent and that said Letters Patent is hereby corrected as shown below:

In the Specification:
Column 1, STATEMENT OF GOVERNMENT SUPPORT, Lines 19-24: Please delete the entire paragraph and replace it with the following:

-- This invention was made with government support under GM-078233 and HL-069757 awarded by the National Institutes of Health. The government has certain rights in the invention. --

Signed and Sealed this
Sixteenth Day of September, 2014

Michelle K. Lee
*Deputy Director of the United States Patent and Trademark Office*